United States Patent
Kohl et al.

(10) Patent No.: US 6,436,649 B1
(45) Date of Patent: Aug. 20, 2002

(54) METHOD FOR DETECTING AND/OR QUANTIFYING A HAPTEN IN A HOMOGENEOUS PHASE AND DEVICE FOR IMPLEMENTATION THEREOF

(75) Inventors: Michel Kohl, Liege; Roger Renotte, Oreye; Gianangelo Ghitti, Liege; Guy Sarlet, Seraing; Robert Lejeune, Heusy, all of (BE)

(73) Assignee: Le Region Wallone, Brussels (BE)

( * ) Notice: Subject to any disclaimer, the term of this patent is extended or adjusted under 35 U.S.C. 154(b) by 0 days.

(21) Appl. No.: 09/171,819

(22) PCT Filed: Apr. 30, 1997

(86) PCT No.: PCT/BE97/00052

§ 371 (c)(1),
(2), (4) Date: Jun. 11, 1999

(87) PCT Pub. No.: WO97/41435

PCT Pub. Date: Nov. 6, 1997

(30) Foreign Application Priority Data

Apr. 30, 1996 (BE) ............................................ 96/00384

(51) Int. Cl.$^7$ ..................... G01N 33/58; C12Q 1/34; C12Q 1/02; C12N 9/96
(52) U.S. Cl. ................. 435/7.1; 435/4; 435/5; 435/7; 435/7.1; 435/7.21; 435/6; 435/18; 435/29; 435/34; 435/38; 435/39; 435/188; 435/805; 435/810; 436/65; 436/88; 436/170; 436/529; 436/530; 436/531; 436/526; 436/527; 436/535; 436/510; 436/814; 422/56; 422/60
(58) Field of Search .................... 435/4, 5, 7, 7.1, 435/7.21, 6, 18, 805, 810, 29.34, 38, 39, 188; 436/65, 88, 170, 529, 530, 531, 526, 527, 535, 510, 814; 422/56, 60

(56) References Cited

U.S. PATENT DOCUMENTS 4,764,462 A 8/1988 Bredehorst et al. ............ 435/18
5,876,944 A * 3/1999 Kuo ............................ 435/7.1

FOREIGN PATENT DOCUMENTS

BE 850647 7/1977

(List continued on next page.)

OTHER PUBLICATIONS

Degand et al., "Enzyme immunoassay screening procedure for the sythetic anabolic estrogens and androgens diethylstilbestrol, nortestosterone, methyltestosterone and trenbolone in bovine urine." Journal of Chromatography, 489, 1989, pp. 235–243, 1989.*

(List continued on next page.)

Primary Examiner—Christopher L. Chin
Assistant Examiner—Lisa V Cook
(74) Attorney, Agent, or Firm—Merchant & Gould P.C.

(57) ABSTRACT

The invention discloses a method for detecting and/or quantifying a hapten in a homogeneous phase, comprising the following steps: adding a known quantity of a hapten inhibitor complex to the solution containing the hapten to be detected and/or quantified; adding to the solution a quantity of antibodies corresponding to the quantity of the hapten/inhibitor complex; adding to the solution a type C β-lactamase having an active site for two substrates in antigenic competition in the said active site, the first substrate being a reporter substrate capable of being transformed into a detectable and/or quantifiable product, preferably by visible UV radiation measurement, the second substrate being the hapten/inhibitor complex acting on the hydrolysis rate of the reporter substrate; detecting and/or quantifying the concentration of the product resulting from the transformation of the reporter substrate, the $K_m$ constant of the reporter substrate being at least a hundred times higher than the $K_m$ constant of the hapten/inhibitor complex, and the $k_{cat}$ constant being at least ten times higher than the $K_{cat}$ constant of the hapten/inhibitor complex.

11 Claims, 15 Drawing Sheets

FOREIGN PATENT DOCUMENTS

| EP | 0 117 648 | 9/1984 | ............ G01N/33/54 |
| EP | 532 187 A1 * | 3/1993 | ............ G01N/33/58 |
| EP | 0 532 187 | 3/1993 | ............ G01N/33/58 |
| EP | 0 532 187 A1 * | 3/1993 | ............ G01N/33/58 |

OTHER PUBLICATIONS

Normark et al., "Chromosal beta–lactam resistance in enterobacteria." Scand. J. Infect. Dis., Suppl. (1986), 49 (IInt. Symp. Ecol. Impacts Antibact. Agents), 38–45 Abstract Only, 1986.*

Takesue et al., "Beta lactamase in gram–negative rods the relationship between penicillinase and R plasmids in gram–negative rods." Hiroshima Journal of Medical Science, (1990) (3),65–70 Abstract Onily.*

Labia et al., "Kinetic studies of beta–lactamase by computerized microacidimetric method.", Biochimica et Biophysica Acta, 384, 1975, 242–249.*

Labia et al., "Kinetic studies of beta–lactamase by computerized microacidimetric method.", Biochimica et Biophysica Acta, 384, 1975, 242–249.*

Degand et al., "Enzyme Immunoassay Screening procedure for the synthetic anabolic estrogens and androgens diethylstilbestrol . . . " Journal of Chromatogrphy, 489 (1989) pp. 235–243.*

Normark et al., "Chromosomal beta–lactam resistance in enterobacteria." Scandanavian Journal of Infection, Dis., Suppl. (19860, 49 (int. Symp. Ecol. Impacts Antibact. Agents), pp. 38–45, Abstract Only.*

Takesus et al., Beta lactamase in gram–negative rods the relationship between pencillinase and r plasmids in gram–negative rods. Hiroshima Journal of Medical Science (1990) 39(3) pp. 65–70, Abstract Only.*

Labia et al., "kinetic studies of a beta–lactamase by a computerized microacidmetric method." Biochimica et Biophysica Acta, 384 (1975) pp. 242–249.*

Wouters et al., "Expression, purification, crystallization and preliminary X–ray analysis of the native class C β–lactamase from *Enterobacter cloacae* 908R and two mutants," *Acta. Cryst.* D57: 162–164 (2001).

Oefner et al., "Refined crystal structure of β–lactamase from *Citrobacter freundii* indicates a mechanism for β–lactam hydrolysis," *Nature*, 343: 284–288 (Jan. 1990).

Lobkovsky et al., "Evolution of an enzyme activity: crystallographic structure at 2–Å resolution of cephalosporinase from the ampC gene of *Enterobacter cloacae* P99 and comparison with a class A penicillinase," *Proc. Natl. Acad. Sci. USA*, 90: 11257–11261 (Dec. 1993).

Edlund et al., "Isolation and characterization of DNA repetitions carrying the chromosomal β–lactamase gene of *Escherichia coli* K–12," *Molec. gen. Genet.*, 173: 115–125 (1979).

Voller et al., 'Enzyme Immunoassays,' *Alternative Immunoassays*, pp. 77–86 (1985).

Henderson et al., 'CEDIA, a New Homogeneous Immunoassay System,' *Clinical Chemistry*, vol. 32, No. 9, pp. 1637–1641 (1986).

* cited by examiner

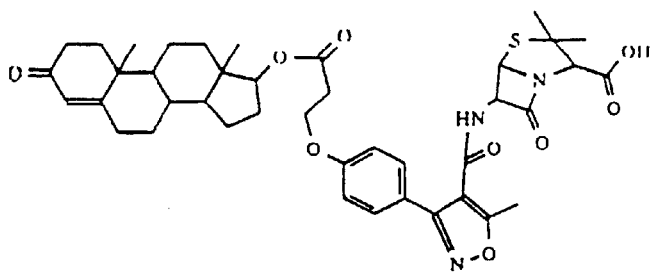
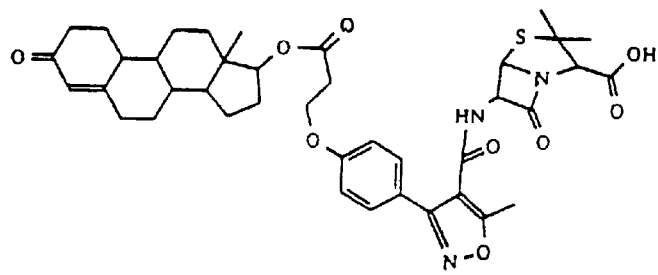
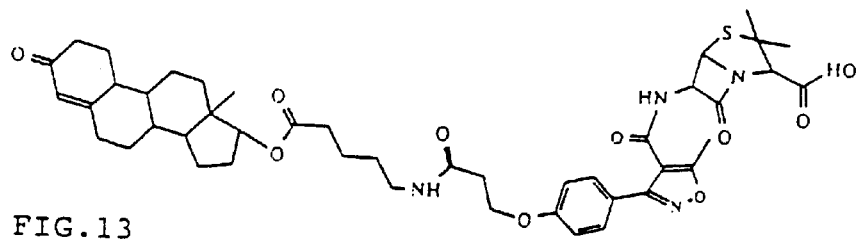
FIG.13
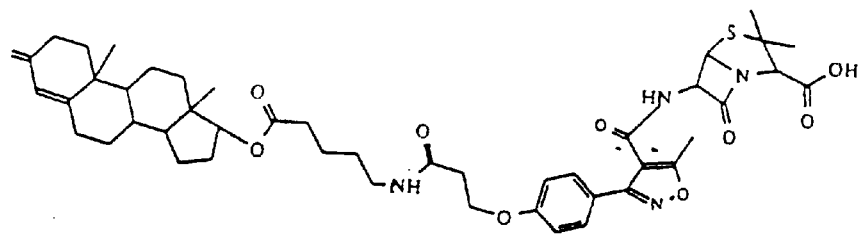
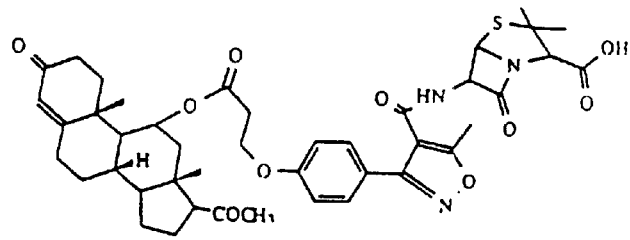
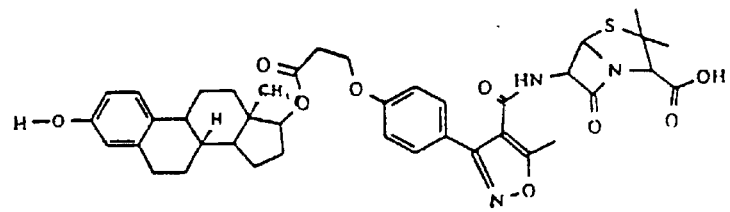

1) E+S : [Enz.] = 0.25 µM
   [S] = 60 µM

2) E+S+I : as 1 + inhibitor (0.24 µM)

3) E+S+I+Ab : as 2 + antibody (serum diluted 625 x)

4) E+S+I+Ab+Analyte : as 3 + nandrolone (from 0.05 to 0.24 µM)

METHOD FOR DETECTING AND/OR QUANTIFYING A HAPTEN IN A HOMOGENEOUS PHASE AND DEVICE FOR IMPLEMENTATION THEREOF

This Application is a National Stage filing under 35 U.S.C. §371 of PCT Application PCT/BE97/00052, filed Apr. 30, 1997, which claims priority under 35 U.S.C. §119 to Belgian Application Ser. No. 96/00,384, filed Apr. 30, 1996.

FIELD OF THE INVENTION

The present invention relates to a method for detecting and/or quantifying a hapten in a homogeneous phase, as well as the device for detection and/or quantification, in particular the kit allowing the screening and/or the assay of a hapten in a homogeneous phase.

BACKGROUND

During the past few years, major advances in the field of biotechnology have made it possible to develop immunoassays allowing the assay of haptens in a homogeneous phase, that is to say of small-sized molecules of natural origin or which are obtained by the synthetic route and which are used in particular for treating animals or humans.

Such molecules may be, for example, active components of medicaments, hormones, anabolic steroids and the like.

To facilitate the application of the tests for screening and/or assaying these haptens, attempts have been made to develop immunoassays which can be used in a homogeneous phase.

Enzymatic immunoassays have thus been proposed. They are "substrate labelled fluorescent immunoassay", "apoenzyme reactivation immunoassay system", "enzyme multiplied immunoassay test" and "enzyme channeling immunoassay" described by Voller and Bidwell (Voller A., Bidwell D. W., in Alternative Immunoassays, Collins W P Ed. John Wiley, Chichester, pp. 78–79 (1986)) as well as the cloned enzyme donor immunoassay (Henderson et al., Cli. Chem., 32, 9, pp. 1637–1641 (1986)).

Patent Application EP-0117648 describes an immunoassay of steroids in phase based on the inhibition of the clotting of milk, this assay giving information on the fertility of milk-producing domestic animals.

However, to date, no success has been achieved in developing, immunoassays working in a homogeneous phase which are sufficiently sensitive, specific and reproducible to allow their widespread use in the assay and/or detection of a large number of haptens in clinical biology and in various media (blood, urine and the like).

The iodine-based systems used up until now have the disadvantage that practically all iodides are oxidizable in the air, generating iodine which is lost by sublimation. This therefore constitutes a first source of instability. Moreover, starch paste is easily degraded by bacteria or fungi, which constitutes another source of instability.

Patent Application FR-2,339,172 describes a reactive system for determining if uric acid or another material oxidizable by iodine exists in a liquid in a proportion greater than a predetermined quantity in an alkaline medium, said reagent comprising a water-activatable iodine generator capable of liberating in situ an appropriate quantity of free iodine with an indicator to detect the presence of iodine. The iodine generator and the indicator are applied to a test strip. Consequently, such a device only works in the dry state and therefore remains dependent on an analysis on a solid system.

SUMMARY OF THE INVENTION

The present invention aims to obtain a method and a device for screening and/or assaying a hapten in any type of homogeneous phase (blood, serum, urine, milk and the like) which are sufficiently sensitive, specific and reproducible.

In particular, it is sought to obtain a method and a device which make it possible in particular to detect haptens present in a human or animal physiological fluid, at concentrations of the order of 100 pM or higher, or even at concentrations of the order of 10 pM or higher.

A specific aim of the present invention seeks to optimize the sensitivity of said method and device by reducing the "background noise" observed in the devices and methods of the state of the art.

A final aim of the present invention seeks to obtain a device which would be capable of being stored for a longer period without contamination or degradation.

BRIEF DESCRIPTION OF THE DRAWINGS

FIG. 13 shows carbenicillin and oxacillin conjugates.

DETAILED DESCRIPTION OF THE INVENTION

The present invention relates to a method for detecting and/or quantifying a hapten in a homogeneous phase, in which:

a known quantity of an inhibitor-hapten complex is added to the solution containing the hapten to be detected and/or to be quantified;

a quantity of antibody corresponding to the quantity of the inhibitor-hapten complex is added to the solution;

a type C β-lactamase having an active site for two substrates entering into competition on said active site is added to the solution, the first substrate being a reporter substrate capable of being transformed into a product which is detectable and/or quantifiable, preferably by visible UV radiation measurement, the second substrate being the inhibitor-hapten complex acting on the rate of hydrolysis of the reporter substrate;

the concentration of the product resulting from the transformation of the reporter substrate is detected and/or quantified, the $k_m$ constant for the reporter substrate being at least 100 times higher, preferably 10,000 times higher, than the $k_m$ constant for the inhibitor-hapten complex, and the $k_{cat}$ constant for the reporter substrate being at least 10 times higher, preferably 10,000 times higher, than the $k_{cat}$ constant for the inhibitor-hapten complex.

Prior to the abovementioned operations, substances may be optionally added to the solution containing the hapten to be assayed in order to remove possible interference such as agents for protecting the enzyme, agents for protecting the reporter substrate, agents for protecting the hapten-inhibitor complex or decontaminating agents and the like.

The abovementioned addition of a quantity of antibody to the solution may be combined with an operation of addition of a reporter substrate to the solution. Some or all of the abovementioned operations may be combined, that is to say may be carried out simultaneously, and/or the indicated order of the operations can be modified.

It is therefore solely for clarity in the description that the different operations prior to the addition of an enzyme to the solution are presented in succession as separate steps.

Consequently, in the absence of free hapten, all the inhibitor-hapten complex molecules will have bound an antibody and will consequently be inactive. The enzymatic activity will consequently be maximum. On the other hand, the higher the quantity of hapten to be assayed, the lower the quantity of inhibitor-hapten-antibody complex, which implies a substantial availability of the molecules of inhibitor-hapten complex.

Figure 1:
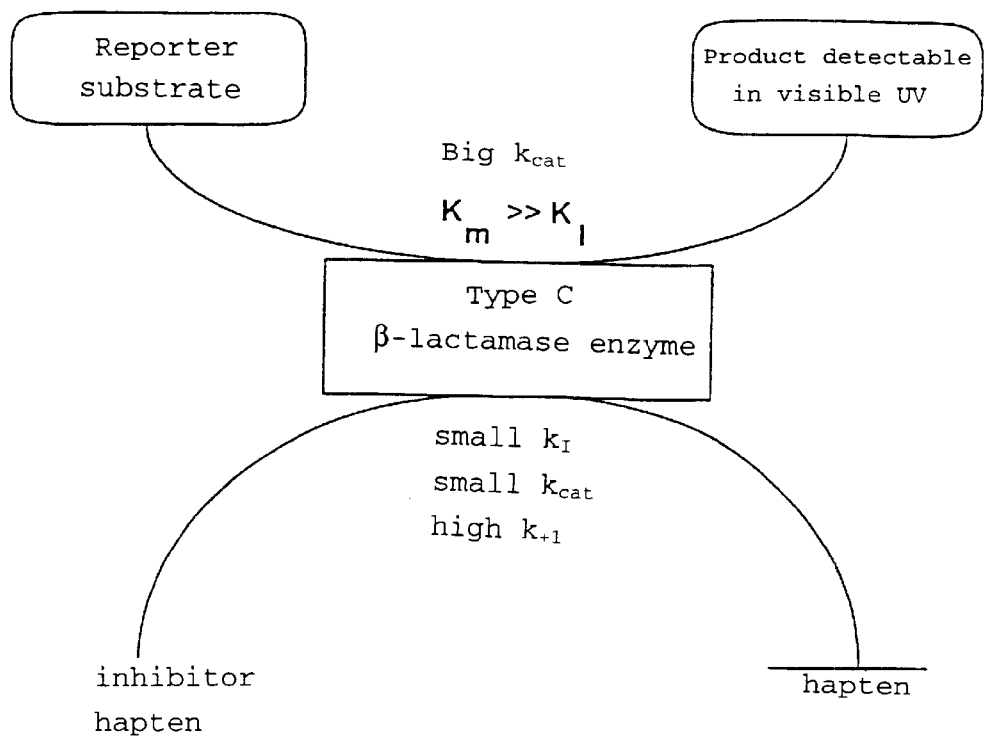
FIG. 1 is the overall scheme.

This will lead to a low enzymatic activity, which will result in a low transformation of the reporter substrate, which will be detected and/or quantified by the low absorption of visible UV radiation (see FIG. 1).

The present invention also relates to the device for screening and/or quantifying a hapten in a homogeneous phase, comprising an enzyme having an active site for two substrates entering into competition on said active site, as well as the two substrates, the first substrate being a reporter substrate capable of being transformed into a product which is detectable and/or quantifiable, preferably by visible UV radiation measurement, the second substrate being an inhibitor-hapten complex modulating the rate of hydrolysis of the reporter substrate. Said device also comprises antibodies capable of binding said inhibitor-hapten complex.

The $k_{cat}$ constant for the reporter substrate is high, greater than 0.1 s$^{-1}$, preferably greater than 10 s$^{-1}$. The $K_i$ constant for the inhibitor-hapten complex is low, less than 5000 µm [sic], preferably less than 100 µm [sic]. The $k_{cat}$ constant for the inhibitor-hapten complex is low, less than 0.1 s$^{-1}$.

In the method and the device according to the invention, the enzyme is a β-lactamase, preferably of type C. Advantageously, the β-lactamase is chosen from the group consisting of β-lactamases obtained from *Enterobacter cloacae* Q908R and P99 and the β-lactamases obtained from *Citrobacter freundii* and *Escherichia coli*.

According to the invention, the inhibitor and the reporter substrate are chosen from the group consisting of the penicillins, the cephalosporins and the β-lactam antibiotics.

The reporter substrate is preferably chosen from the group consisting of cephaloridine, nitrocefin, cephalothin, cephalexin, cephalosporin C, cephacetrile and cefazolin.

According to the invention, the inhibitor of the inhibitor-hapten complex is preferably chosen from the group consisting of carbenicillin, oxacillin, cefuroxine, cefotaxime and methicillin.

The invention also relates to a method of detection by a color system using an iodine/starch paste system stabilized by addition of cadmium iodide.

Preferably, the demonstration of the reaction of the reporter substrate is detected by measuring the color specific to the hydrolysis products or, when these products are not colored, by an indicator system, in particular by coloring with iodine/starch.

The Applicant noticed that cadmium iodide is stable to oxidation in the air and that the toxic properties of the cadmium ion stabilize starch paste to pollution by microorganisms.

A system of the type mentioned, based on the generation of iodine in a starch paste solution stabilized by addition of cadmium iodide, proved particularly favorable in the abovementioned technique.

Cadmium iodide, in the presence of DTPA and iodate, reacts in a medium of pH 2 to produce the reagent which can then be brought to the working pH.

It should be noted that this type of reaction may also be suitable for other assays, such as the assay of cephalexin with iodine, as will be described in an exemplary embodiment below.

In the particular case of the detection and/or the quantification (assay) of the concentration of the product resulting from the transformation of the reporter substrate which was mentioned above, this starch/iodine color allows the detection and/or the assay of a hapten at low concentrations and in a range of colors which discriminates with respect to the general color of the homogeneous phase.

In the method and the device according to the invention, the inhibitor is preferably chosen from the group consisting of carbenicillin, oxacillin, cefuroxine, cefotaxime and methicillin, as well as any other substance with a β-lactam ring or a ring related to the β-lactam ring, or even any substance not necessarily possessing a β-lactam ring or a ring related to the β-lactam ring but exhibiting measurable kinetic parameters ($K_m$, $K_i$ and $k_{cat}$) toward the abovementioned enzyme group and ensuring a slowing down of the rate of hydrolysis of the reporter substrate.

Advantageously, the hapten to be assayed is a medicament active component, a hormone, an anabolic steroid or a drug which is preferably chosen from the group consisting of testosterone, estridiol [sic], progesterone, aldosterone, cortisol, methylamphetamine, methadone, tetrahydrocannabinol, $\Delta^4$-androstenedione, morphine, DHEA sulfate, nandrolone, theophylline, cocaine and/or their hydrolysis derivatives.

DESCRIPTION OF A PREFERRED EMBODIMENT OF THE INVENTION

1. Choice of the Enzyme

β-Lactamases can be grouped into four families: A, B, C and D. Those of the A, C and D types are characterized by their mode of action which involves the formation of an acyl-enzyme complex via an active site comprising a serine. The C type enzymes were advantageously selected on the basis:

of the kinetic parameters known from the literature,
of their reaction scheme in the presence of an inhibitor,
of their commercial availability,
of their chemical and thermal stability.

Practically no clear-cut inhibitors exist in the reactions of hydrolysis of penicillin by type C β-lactamases. The terms "good and poor substrate" are consequently used to characterize penicillins in their interactions with the β-lactamases. However, for the sake of simplicity, the terms "substrate" and "inhibitor" will be used in the remainder of the document.

A good substrate or reporter substrate will be used jointly with a poor substrate, that is to say with the hapten-inhibitor complex. The models of inactivation by the latter postulate the formation of a relatively stable enzyme-inhibitor complex by the formation of an acyl enzyme.

Among the β-lactamases which can be used, there may be mentioned the β-lactamases from *Enterobacter cloacae* Q908R and P99, from *Citrobacter freundii* or from *Escherichia coli*.

2. Choice of the Inhibitor

The choice of the inhibitor depends on the kinetic parameters and on the possibilities of coupling with the hapten to be assayed (presence of functional groups which are not essential for the inhibitory activity). At the enzymatic level, the ideal inhibitor should have a $k_{cat}$ which is as low as possible (very slow rate of degradation) while having a $K_m$ which is as low as possible (high affinity for the enzyme). In the case of the inhibition reactions envisaged, the $K_m$ value is close to the constant $K_i$. The $K_m$ can therefore be estimated from an evaluation of the $K_i$. This is obtained from kinetic measurements carried out in the presence of a reporter substrate with known characteristics, and this in the presence of a variable quantity of inhibitor. The ideal inhibitor should also have a rate constant $k_{+1}$ (corresponding to the step of binding of the inhibitor to the enzyme) which is as high as possible. Based on this principle, it has been possible to select five inhibitors. They are:

carbenicillin ($K_m$=0.5 to 20 nM; $k_{cat}$=0.002 to 0.004 s$^{-1}$),
oxacillin ($K_m$=0.5 nN; $k_{cat}$=0.005 s$^{-1}$),
cefuroxine ($K_m$=20 nM; $k_{cat}$=0.04 to 0.15 s$^{-1}$),
cefotaxime ($K_m$=20 to 170 nM; $k_{cat}$=0.01 to 0.17 s$^{-1}$),
methicillin ($K_m$=2 to 150 nM; $k_{cat}$=0.007 to 0.08 s$^{-1}$).

The inhibitor should have at least one chemical function which is free and nonessential for its inhibitory activity allowing its coupling to the hapten to be assayed.

The inhibitor used should furthermore be capable of being coupled to a steroid such as nandrolone, to a medicament such as theophylline or to a drug such as cocaine.

3. Choice of the Reporter Substrate

The $K_m$ and $k_{cat}$ values for a series of reporter substrates brought into contact with various β-lactamases are assembled in Tables 1 and 2. The data were either experimentally determined, or extracted from data available in the literature.

TABLE I

KINETIC PARAMETERS FOR VARIOUS PENICILLINS IN THE PRESENCE OF β-LACTAMASES

| substrate | Enzyme[1] | $K_m$ (μM) | $k_{cat}$ (S$^{-1}$) | $R_1$ | $R_2$ |
|---|---|---|---|---|---|
| Benzylpenicillin (penicillin G) | P99/Q908R/Citro.F. E. Coli | 0.5 4.4 | 20 45 | —CH$_2$—phenyl | No |
| Oxacillin | P99/Q908E/E. Coli | 0.0005 | 0.005 | phenyl-isoxazole-CH$_3$ | No |
| Ticarcillin | P99/Q908E/E. Coli | 0.25 | 0.045 | thiophene-CH(COOH)— | No |
| Carbenicillin | P99/Q908R Citro.F. E. Coli | 0.01 0.0005 0.02 | 0.002 0.004 0.003 | phenyl-CH(COOH)— | No |

TABLE I-continued

KINETIC PARAMETERS FOR VARIOUS PENICILLINS
IN THE PRESENCE OF β-LACTAMASES

| substrate | Enzyme[1] | $K_m$ (μM) | $k_{cat}$ (S$^{-1}$) | $R_1$ | $R_2$ |
|---|---|---|---|---|---|
| Methicillin | P99/Q908R | 0.03 | 0.007 | 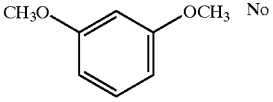 | No |
| | Citro.F. | 0.002 | 0.01 | | |
| | E. Coli | 0.15 | 0.08 | | |

[1]Citro.F. represents a β-lactamase from *Citrobacter freundii* and P99 and Q908R represents β-lactamases obtained from *Enterobacter cloacae*.

TABLE 2

KINETIC PARAMETERS FOR VARIOUS
CEPHALOSPORINS IN THE PRESENCE OF β-LACTAMASES

| substrate | Enzyme | $K_m$ (μM) | $k_{cat}$ (S$^{-1}$) | $R_1$ | $R_2$ |
|---|---|---|---|---|---|
| Cephaloridine | P99/Q908R | 70 | 650 | 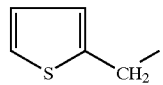 | 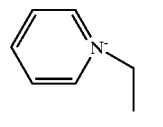 |
| | Citro.F. | 35 | 700 | | |
| | E. Coli | 170 | 130 | | |
| Nitrocephin | P99/Q908R | 25 | 780 | 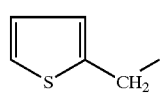 | 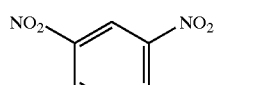 |
| | Citro.F. | 12 | 300 | | |
| | E. Coli | 500 | 500 | | |
| Cephalothin | P99/Q908R | 15 | 200 | 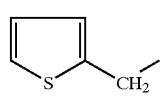 | $CH_3COOCH_2$— |
| | E. Coli | 42 | 300 | | |
| Cephalexin | P99/Q908R | 10 | 100 | 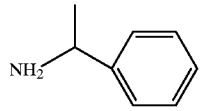 | $CH_3$— |
| | Citro.F. | 12 | 170 | | |
| | E. Coli | 4 | 38 | | |
| Cephalosporin C (penicill. N) | P99/Q908P | 400 | 1100 | 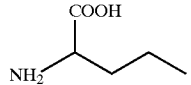 | No |
| Cephaglycine | P99/Q908R | 2 | 1 | 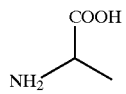 | No |
| Cephaestrile | P99/Q908R | 140 | 143 | —$CH_2$—CN | No |
| Cefuroxime | P99/Q908R | 0.02 | 0.04 | 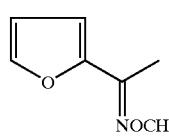 | $NH_2COOCH_2$— |
| | E. Coli | 0.15 | 0.15 | | |
| Cefotaxime | P99/Q908R | 0.01 | 0.01 | 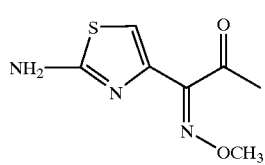 | No |
| | E. Coli | 1.7 | 0.17 | | |

TABLE 2-continued

KINETTC PARAMETERS FOR VARIOUS CEPHALOSPORINS IN THE PRESENCE OF β-LACTAMASES

| substrate | Enzyme | $K_m$ (μM) | $k_{cat}$ (S$^{-1}$) | $R_1$ | $R_2$ |
|---|---|---|---|---|---|
| Cefazolin | P99/Q908R | 600–1500? | 3000 | | |
| | E. Coli | 400 | 150 | | |

It can be observed on reading Tables 1 and 2 that cephaloridine, nitrocefin, cephalotin [sic], cephalosporin C, cephacetrile, cephazolin (but also apholexin) can also be used as reporter substrates.

4. Synthesis of Nandrolone Carbenicillinate (Conjugate 1)

Figure 2:
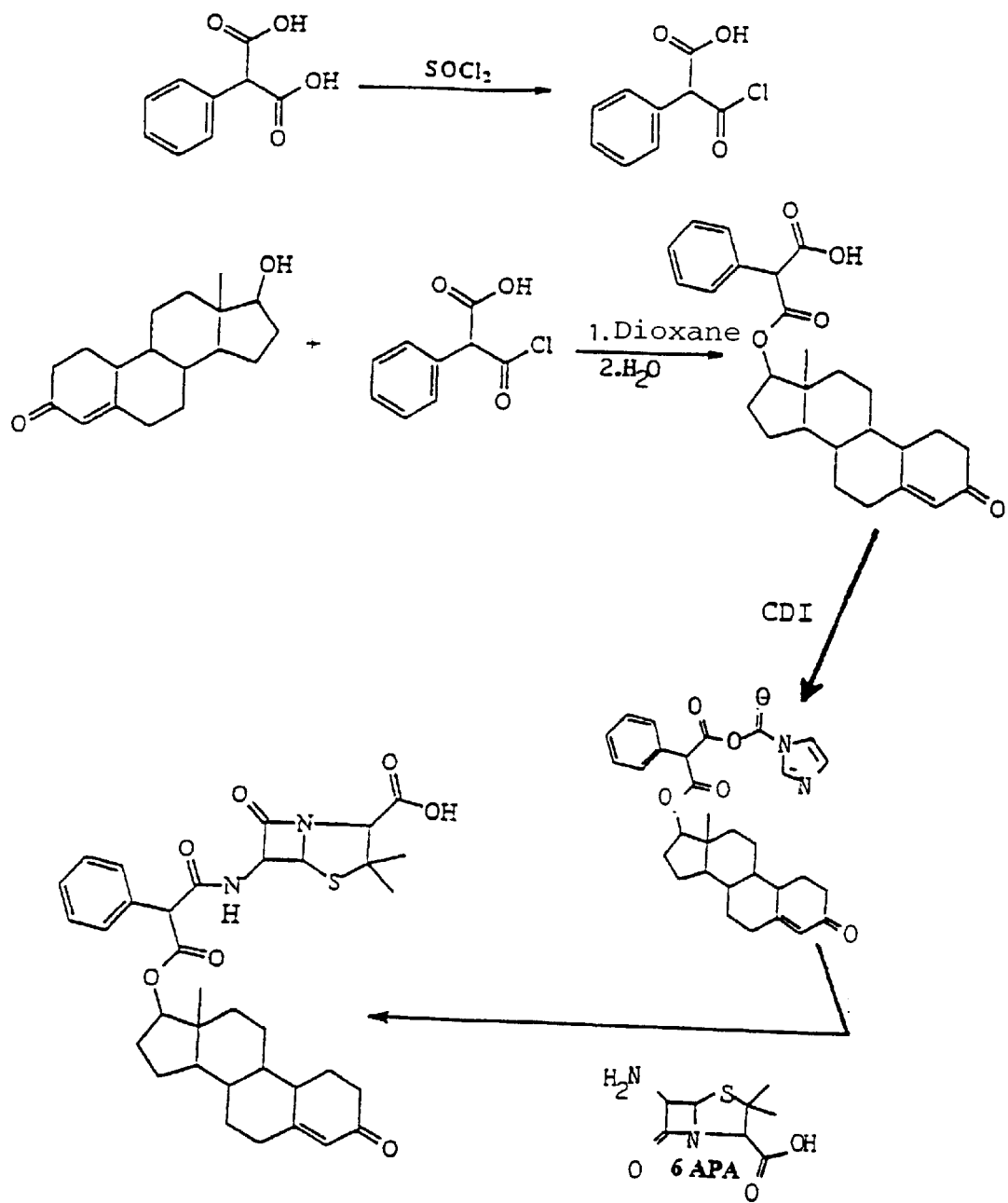
FIG. 2 describes the synthesis of nandrolone carbencillinate (conjugate 1).

Phenylmalonic acid is converted to an acid monochloride by incubation at 35° C. in a dry dioxane-ether mixture with 1.2 equivalents of thionyl chloride for 3 hours. The solvents are evaporated and the residue (hot oil), taken up in a dioxane-ether mixture, is mixed with an ice-cold solution of nandrolone in dioxane. The mixture in which the steroid is deficient is incubated at room temperature for 12 hours. The product is extracted with an aqueous sodium bicarbonate solution, and then after acidification of the solution to pH 2, re-extracted with chloroform. The steroid phenylmalonate is obtained by evaporation of the chloroform (see FIG. 2).

The coupling of the nandrolone phenylmalonate to 6-APA is carried out conventionally after activation with carbonyl-diimidazole (CDI). The purification of the conjugate is obtained by extraction in ether in a medium of pH 2 and 8.5 before final recrystallization from a toluene-white petrolatum mixture (see Table 9).

5. Synthesis of Cocaine Carbenicillinate (Conjugate 2)

Figure 3:
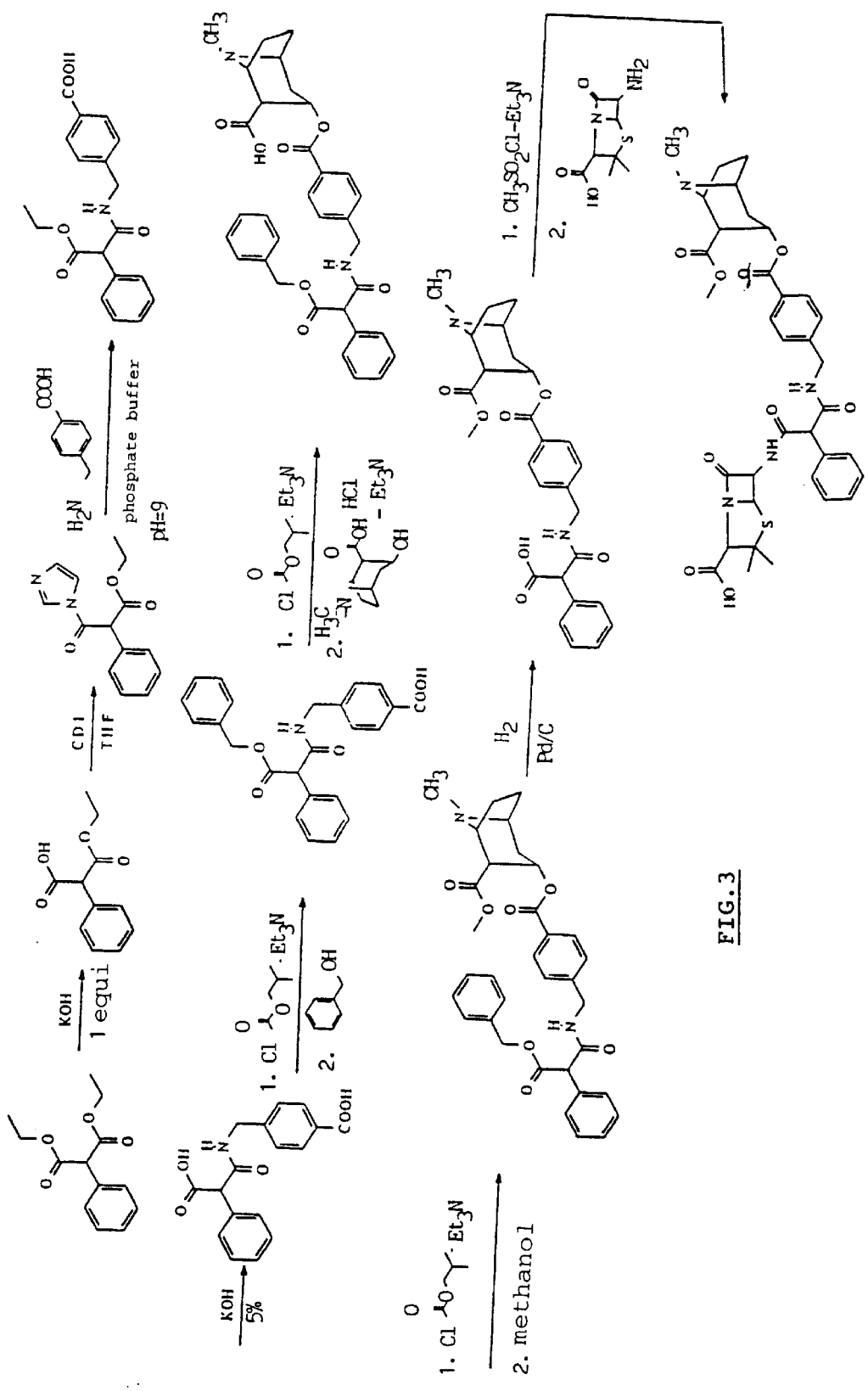
FIG. 3 describes the synthesis of cocaine carbencillinate (conjugate 2).
Figure 4:
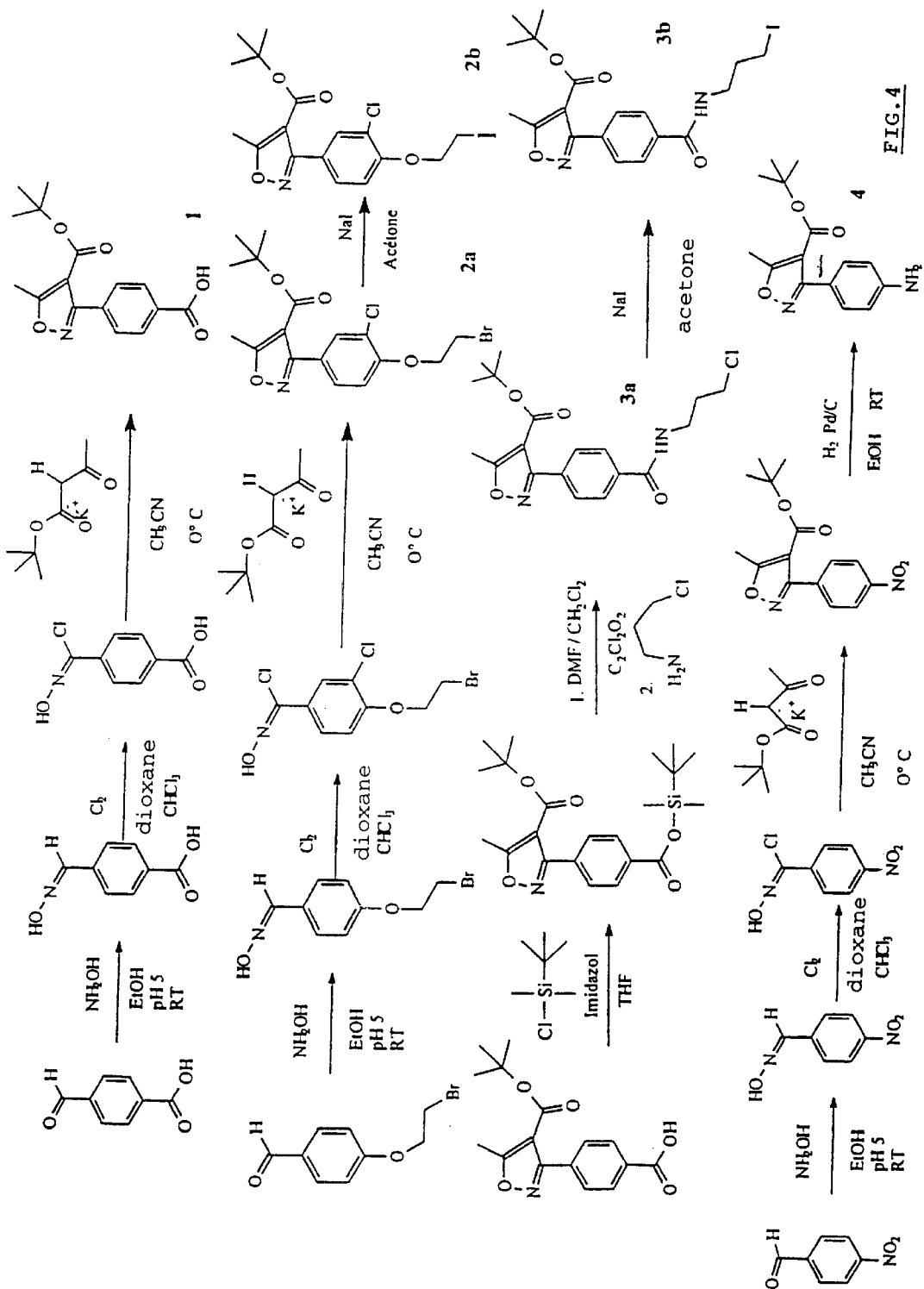
FIG. 4 describes the synthesis of the precursors (phenylisoxazoles).
Figure 5:
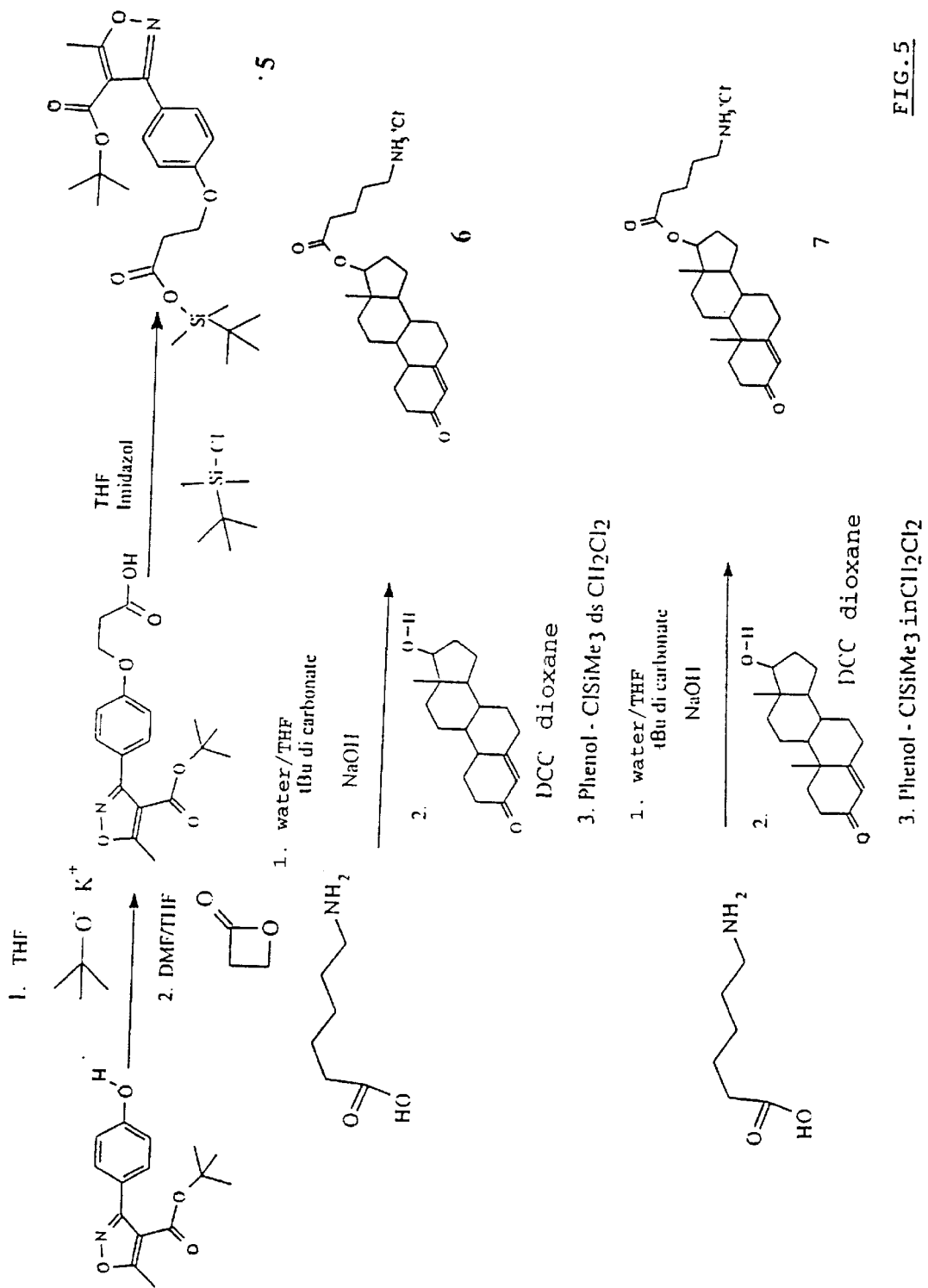
FIG. 5 describes the synthesis of precursors 5, 6, and 7.
Figure 6:
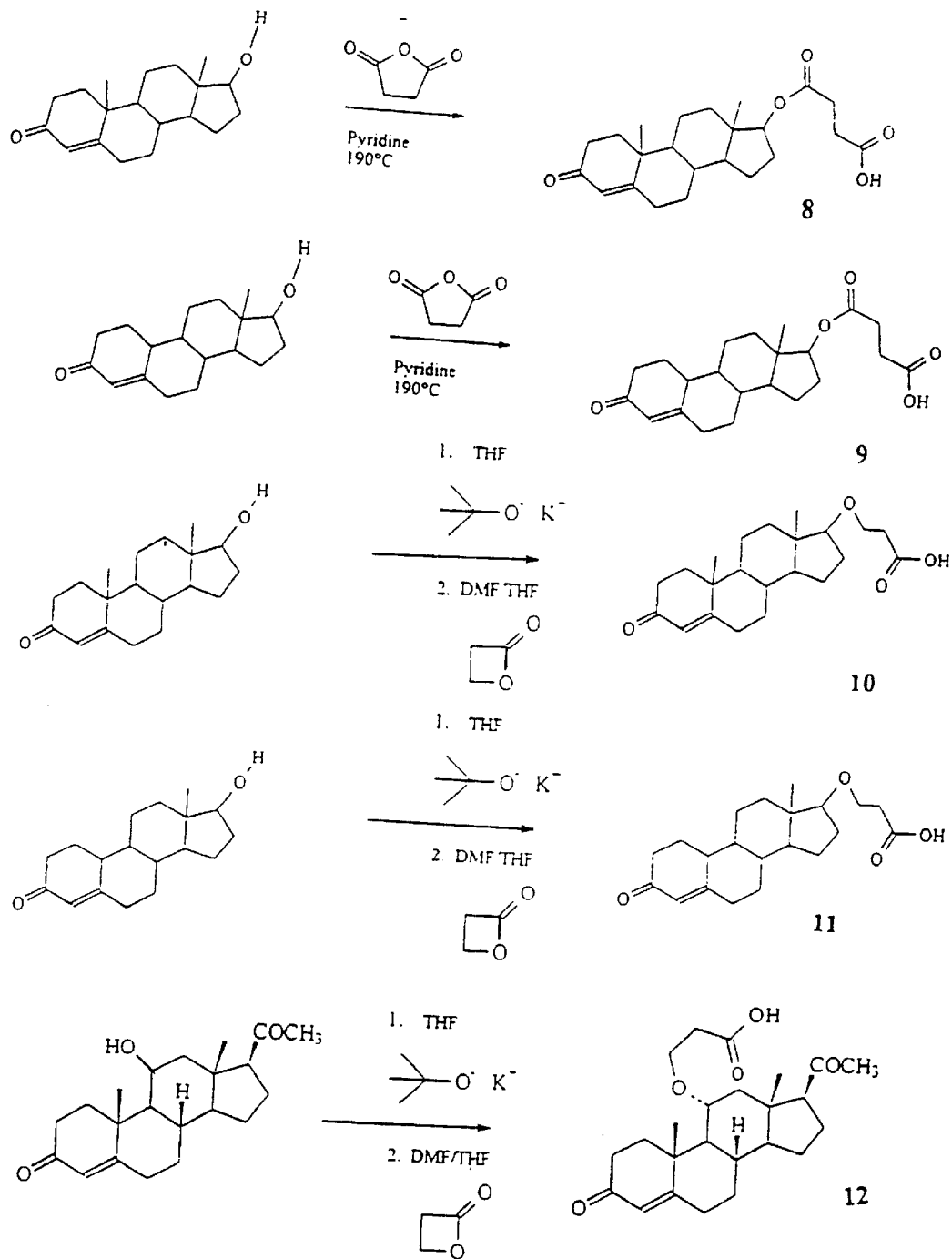
FIG. 6 describes the synthesis of precursors 8, 9, 10, 11, and 12.
Figure 7:
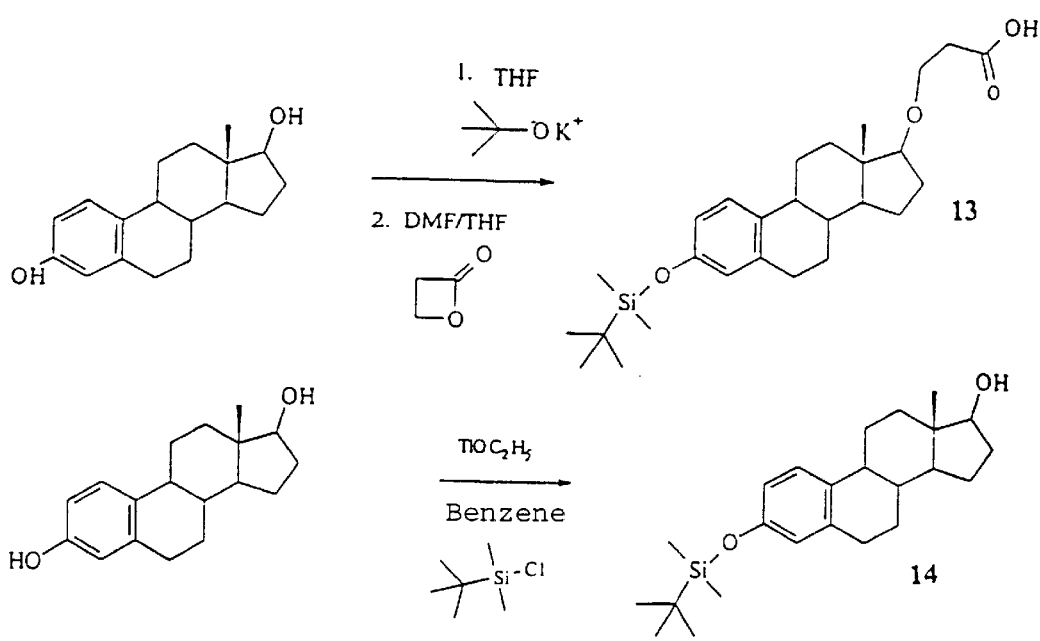
FIG. 7 describes the synthesis of precursors 13 and 14.
Figure 8:
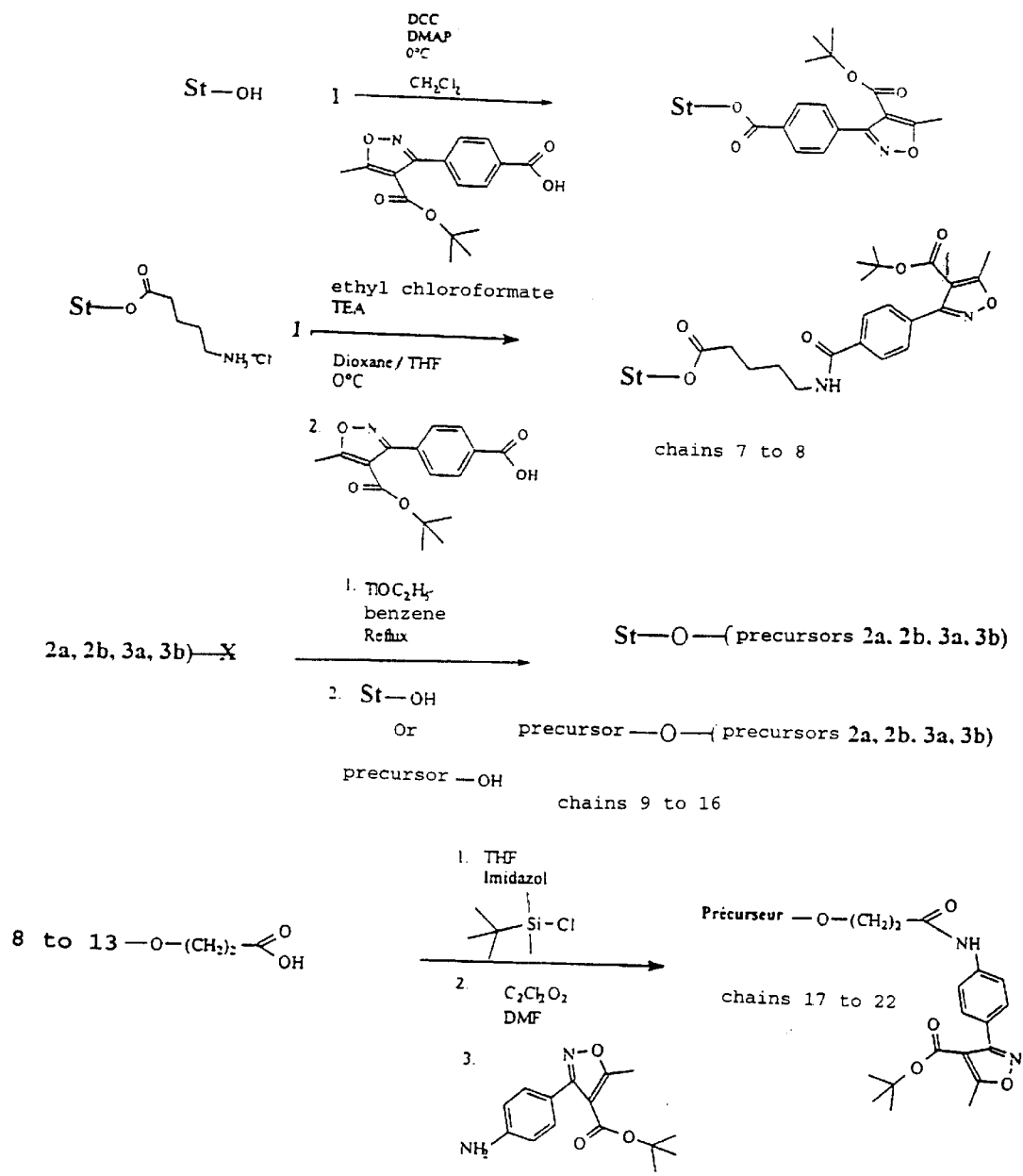
FIG. 8 describes the formation of oxacillin side chains by reacting precursors 1 to 5 with precursors 6 to 14.
Figure 9:
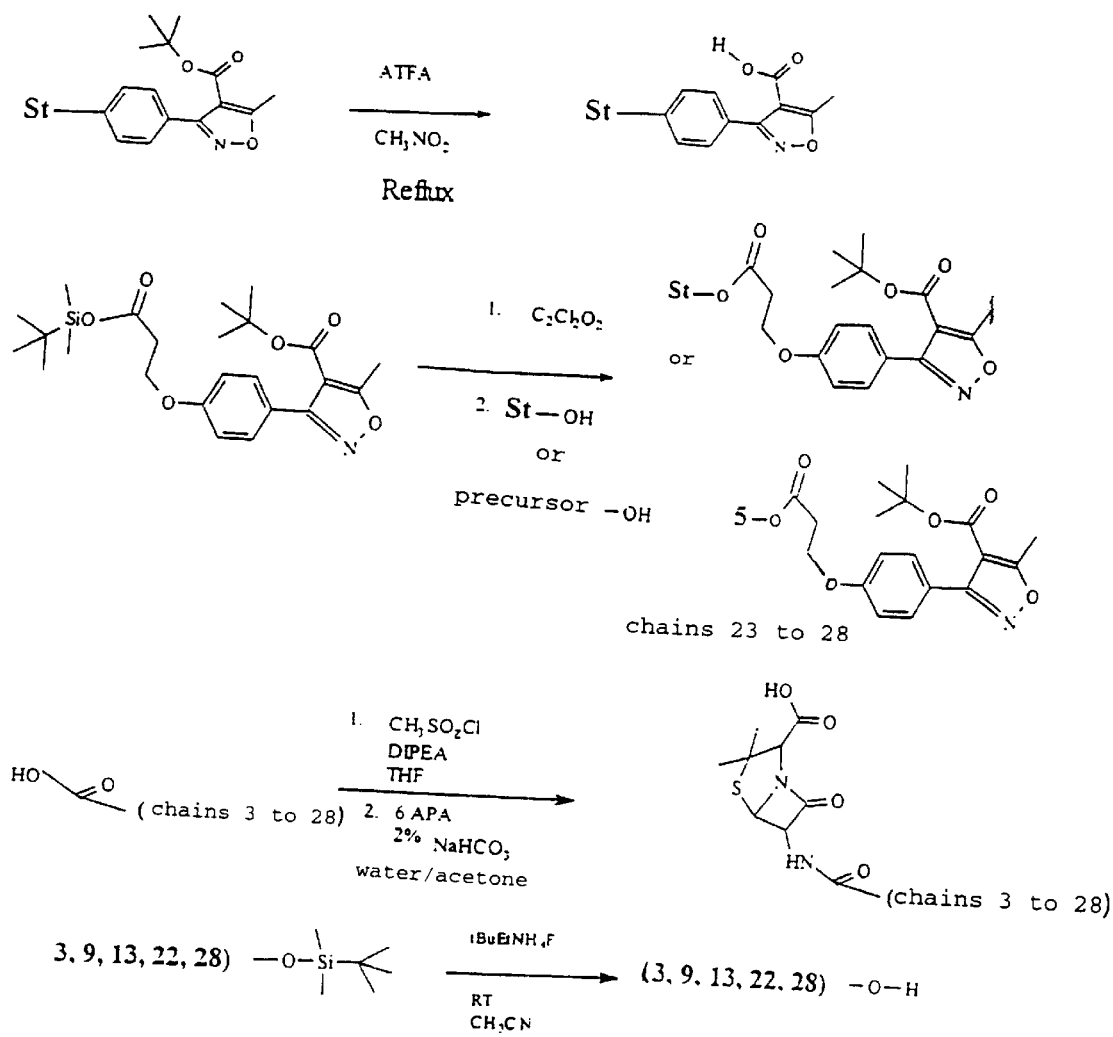
FIG. 9 also describes the formation of oxacillin side chains by reacting precursors 1 to 5 with precursors 6 to 14.
Figure 10:
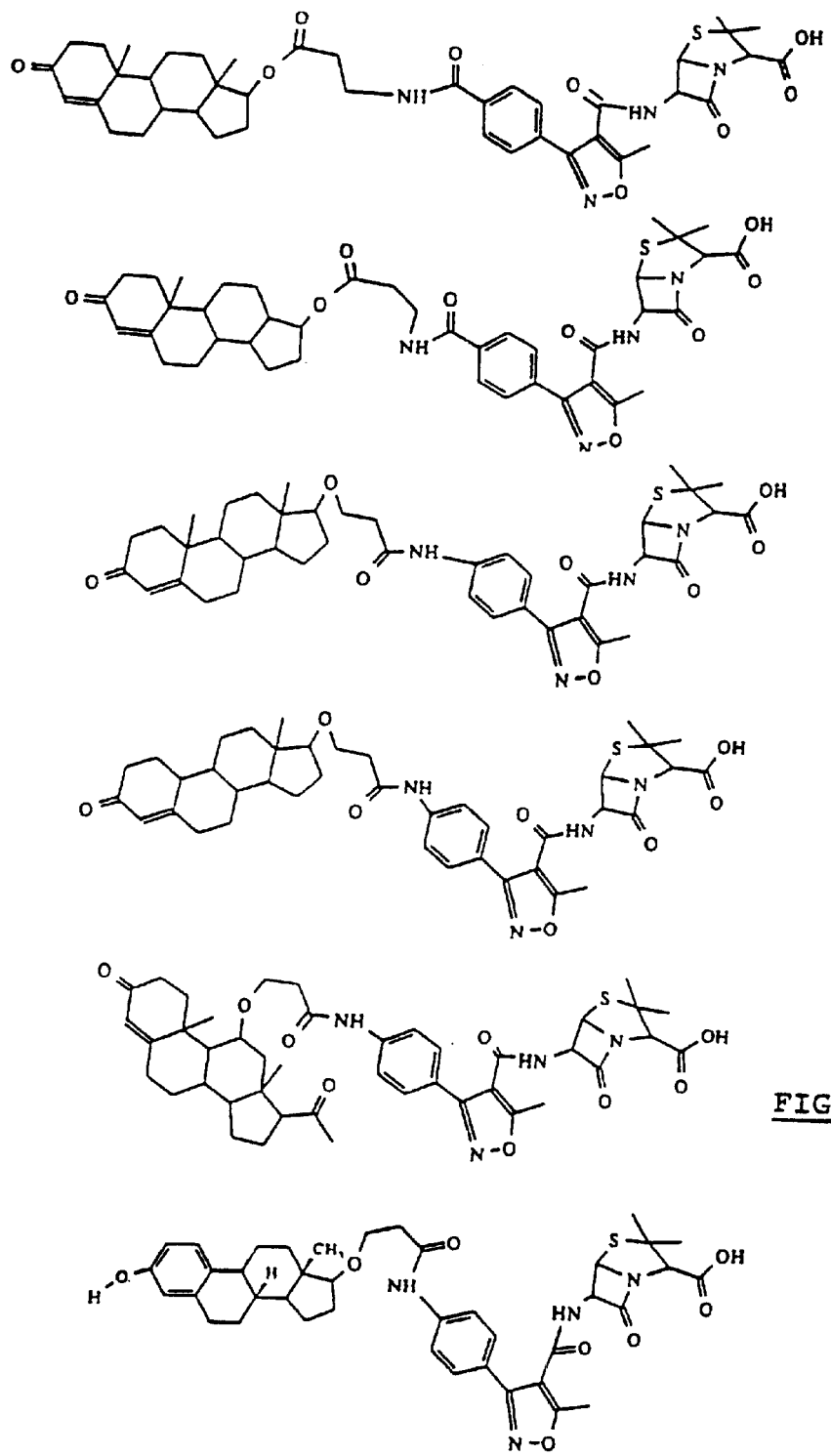
FIG. 10 shows carbenicillin and oxacillin conjugates.
Figure 11:
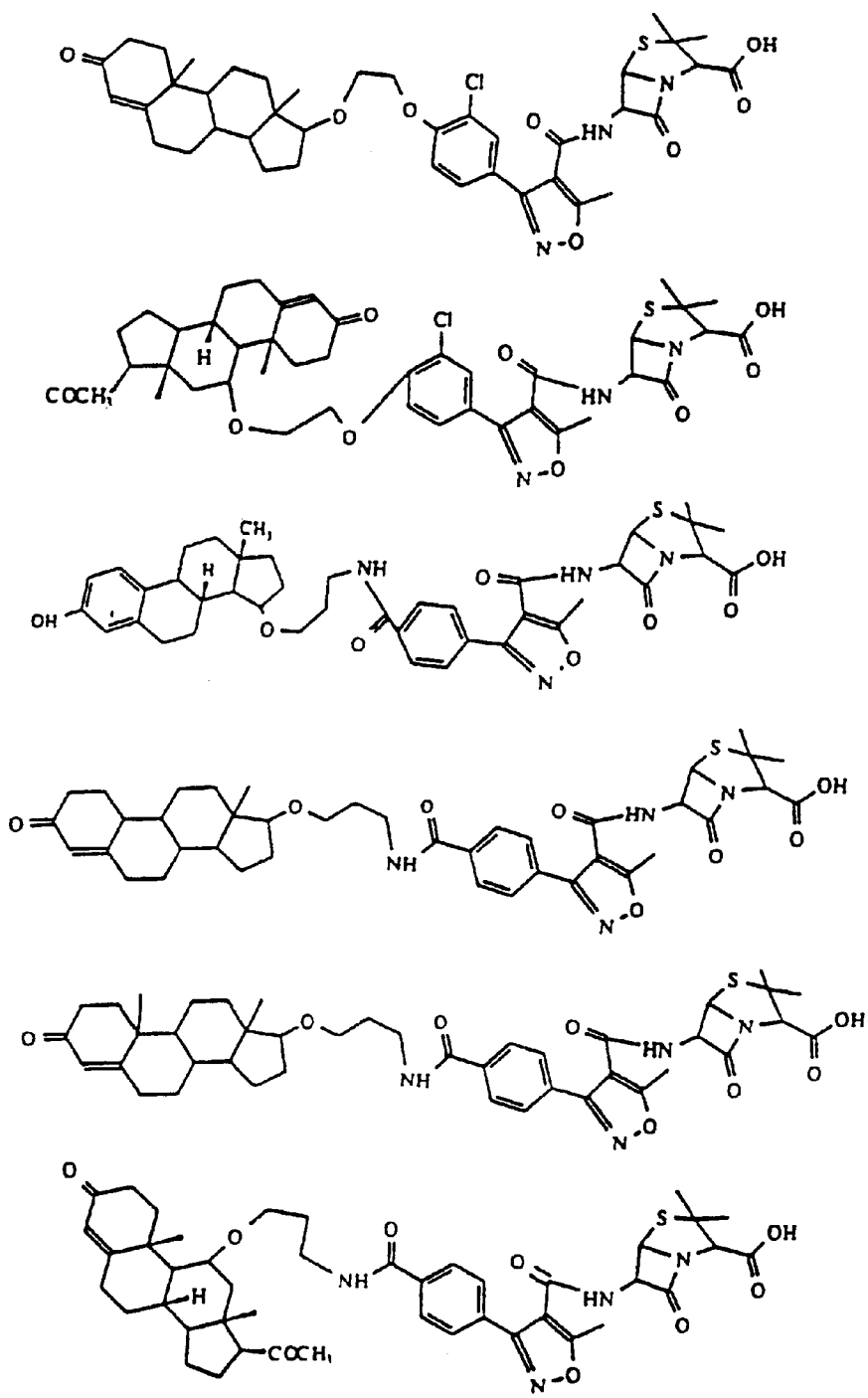
FIG. 11 shows carbenicillin and oxacillin conjugates.
Figure 12:
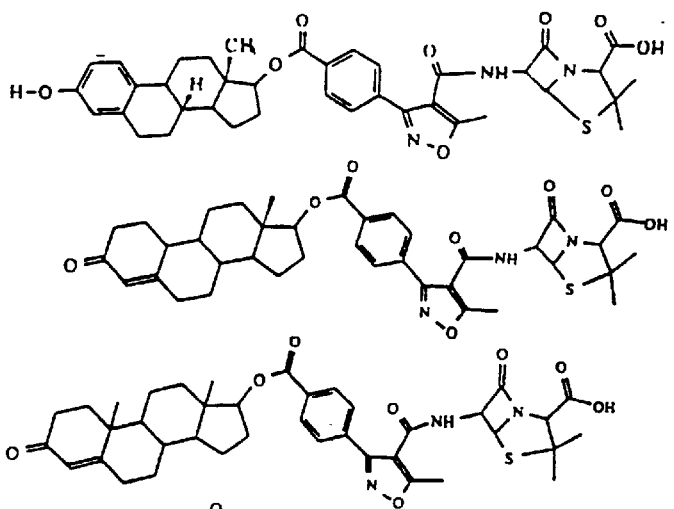
FIG. 12 shows carbenicillin and oxacillin conjugates.
Figure 12:
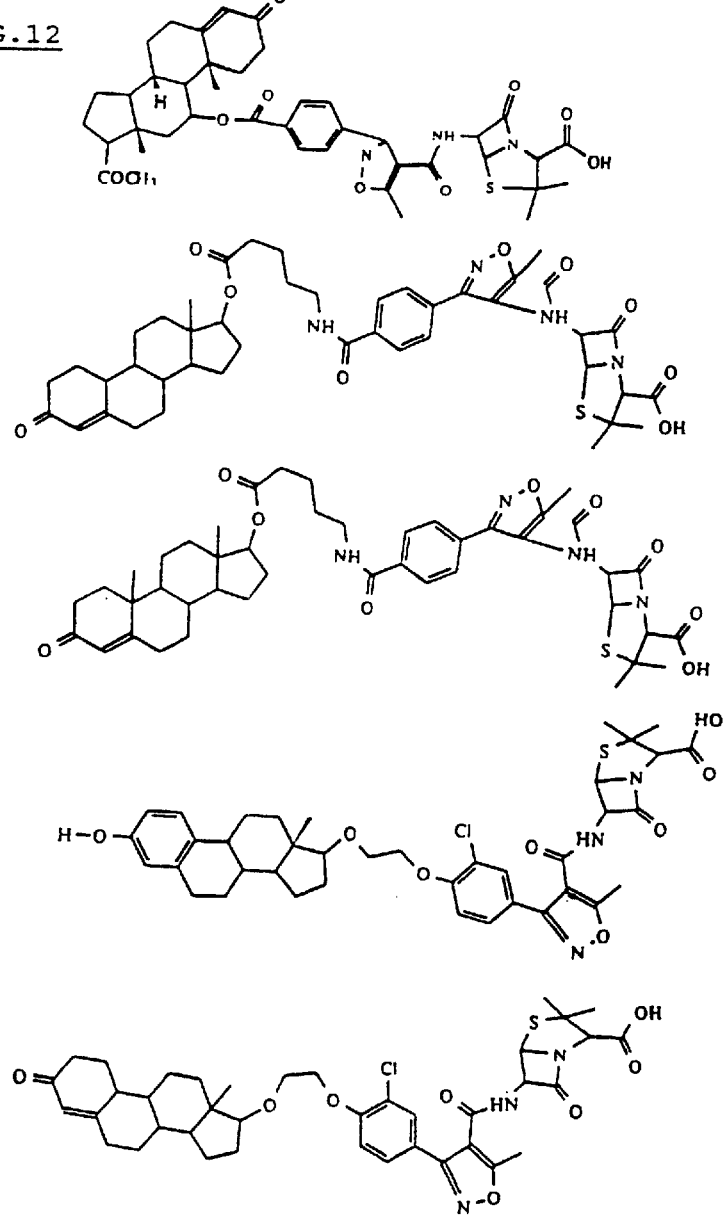

Diethyl phenylmalonate is hydrolyzed to a monoester by the action of one equivalent of KOH in an aqueous-alcoholic medium. The monoester is then conjugated with p-aminomethylbenzoic acid by a conventional procedure involving carboxyl diimidazole as activating agent. The residual ethyl ester is replaced with a corresponding benzyl ester by hydrolysis with 5% KOH followed by esterification with benzyl alcohol using the method of mixed anhydrides with isobutyl chloroformate in the presence of one equivalent of triethylamine. The remaining carboxyl functional group is conventionally activated with isobutyl chloroformate and then coupled to ecgonine. The carboxylic acid of the benzoylecgonine portion of the conjugate is converted by methyl ester by the same technique applied in the presence of methanol. The benzyl functional group is removed by hydrogenolysis in the presence of palladium on carbon at a hydrogen pressure of two bar. The acid generated is used for the final coupling to 6-APA using prior activation with methanesulfonyl chloride according to the method of Brown et al., Chem. Soc. Perkins Trans No. 1, p. 881 (1991) (see FIG. 3). The purification of this compound is obtained by extraction in ether in a medium of pH 2 and 8.5 before final recrystallization from the toluene-white petrolatum mixture (see Table 9).

6. Synthesis of Various Nandrolone Oxacillinates and of Other Steroids

In order to lower the limit of detection of nandrolone and of the other steroids, they are coupled to a more effective inhibitor (having a particularly low $K_i$) and so as to create a range of inhibitors with varying inhibitory properties suited to various uses requiring different levels of inhibitory power. The synthesis of these products is described below. The procedure followed in order to obtain the target molecules consists in synthesizing precursors comprising the steroid portion and the side chain bound to penicillin appropriately modified in order to allow coupling to the steroid and in order to generate significant differences in $K_i$. Next, an amide is formed by coupling the precursor to 6-APA in order to obtain the final molecule. The general method of synthesis presented below is summarized in FIGS. 4 to 13.

6.1. Synthesis of the Precursors (Phenylisoxazoles)

Synthesis of tert-butyl 3-(4-carboxyphenyl)-5-methylisoxazole-4-carboxylate (Precursor 1)

One equivalent of 4-carboxybenzaldehyde (I) is reacted with two equivalents of hydroxylamine hydrochloride in a water/methanol mixture adjusted to pH 4.5 with NaOH. After two hours of reaction, the solution is concentrated under vacuum until precipitation of the product (II) is obtained. The precipitate is filtered, washed with ice-cold water and redissolved in an NaHCO$_3$ buffer at pH 8. The product solution is purified using charcoal, filtered and reacidified with HCl. The product (II) which precipitates is isolated, washed with H$_2$O and dried under vacuum.

The product II is dissolved in a dioxane/CHCl$_3$ mixture. The solution, cooled in an acetone/dry ice mixture, is then saturated with chlorine. The chlorinated solution is then heated gradually up to room temperature. After complete reaction, the solution is evaporated under vacuum. The product obtained (III) is dissolved in ethanol and precipitated by addition of white petrolatum.

One equivalent of product III is dissolved in a methanol/acetonitrile mixture. After cooling to 0° C., two equivalents of Na tert-butyl acetoacetate (IV) are slowly added to the solution of product III. At the end of the reaction, the solution is supplemented with water acidified with acetic acid. The product is extracted from the solution with chloroform. The chloroformic phase, washed with water, is dried over sodium sulfate. It is then evaporated until the product (V) is concentrated.

Synthesis of tert-butyl 3-[4-(2-bromomethoxy)-3-chlorophenyl]-5-methylisoxazole-4-carboxylate and tert-butyl 3-[4-(2-iodoethoxy)-3-chlorophenyl]-5-methyl-isoxazole-4-carboxylate (Precursors 2a and 2b)

The synthesis is based on the preparation of the preceding product, the starting material being bromomethoxybenzaldehyde. The bromomethoxybenzaldehyde is converted to an oxime by the action of hydroxylamine hydrochloride in an aqueous-alcoholic medium whose pH is kept at 5 by controlled addition of NaOH. The action of the chlorine at saturation in chloroform for 2 hours converts the oxime to a chloroxime with subsequent substitution of the phenyl ring with a chlorine atom at the ortho position of the ether. The product is. purified twice by chromatography on a silica column, the mobile phase consisting of toluene, ethyl acetate and acetic acid (6;1;0.1) in order to eliminate the unstable compounds which form during the reaction. The stable compound obtained (Table 9) is then reacted with 1 equivalent of potassium salt of tert-butyl acetoacetate. The addition compound cyclizes during the reaction in order to give tert-butyl 3-[4-(2-bromomethoxy)-3-chlorophenyl]-5-methylisoxazole-4-carboxylate, which can be converted to a corresponding iodinated derivative by reaction with NaI in an acetonic medium.

Synthesis of tert-butyl 3-[N-(3-chloropropyl)
benzamid-4-yl]-5-methylisoxazole-4-carboxylate
and tert-butyl 3-[N-(3-iodopropyl)benzamid-4-yl]-5-
methylisoxazole-4-carboxylate (Precursors 3a and
3b)

The tert-butyl 3-(4-carboxyphenyl)-5-methyl-isoxazole-4-carboxylate is protected by forming a tert-butyldimethylsilyl derivative on the carboxyl functional group by reacting with tert-butyldimethylsilyl chloride in the presence of imidazole. The protected derivative is converted to an acid chloride by the action of oxalyl chloride in a mixture of dimethylformamide and dichloromethane. The acid chloride is then formed by an amide by reacting with the chloropropylamine introduced in the hydrochloride form into the medium containing the acid chloride supplemented with an excess of triethylamine. The chlorinated derivative thus obtained may be converted to the corresponding iodinated derivative by reacting with NaI in acetone.

Synthesis of tert-butyl 3-(4-aminophenyl)-5-
methylisoxazole-4-carboxylate (Precursor 4)

The 4-nitrobenzaldehyde is converted to an oxime by reacting with hydroxylamine in an aqueous-alcoholic medium at pH 5 (maintenance of the pH by addition of KOH), then the chlorooxime is formed by chlorination with the aid of gaseous chlorine in chloroform. The reaction of the derivative obtained with the potassium salt of tert-butyl acetoacetate gives tert-butyl 3-(4-nitrophenyl)-5-methylisoxazole-4-carboxylate, which is reduced with the aid of hydrogen (2 bar) catalyzed by palladium on carbon. The amine-containing derivative is isolated in hydrochloride form in ethyl acetate.

Synthesis of tert-butyl 3-[4-(2-carboxyethoxy)
phenyl]-5-methylisoxazole-4-carboxylate protected
by a tert-butyldimethylsilyl ester (Precursor 5)

para-Hydroxybenzaldehyde is reacted with propiolactone in the presence of potassium tert-butoxide in a mixture of dimethylformamide and acetonitrile. The derivative formed is converted to an oxime as described above for the related compounds and protected by reacting with 1 equivalent of tert-butyl dimethylsilyl chloride for 2 hours in tetrahydrofuran supplemented with imidazole. The action of chlorine on the product gives the chloroxime which is converted to an isoxazole by the potassium salt of tert-butyl acetoacetate according to the method already described.

6.2. Preparation of Steroids for Coupling to
Phenylisoxazoles

Nandrolone and testosterone were used without modification or after addition of a 5-aminovaleric or 3-hydroxypropionic arm.

Aminovaleric Derivatives of Nandrolone (Precursor
6) or of Testesterone [sic] (Precursor 7)

The 5-aminovaleric acid is protected with a Boc group by reaction of di-tert-butyl dicarbonate in a water-tetrahydrofuran mixture in the presence of NaOH. The derivative obtained is but [sic] in reaction with a deficient quantity of testosterone or nandrolone in the presence of a slight excess of dicyclohexylcarbodiimide and of dimethylaminopyridine. The reaction is carried out in a mixture of dioxane and tetrahydrofuran at a temperature of 0° C. The protection of the amine group is removed by reaction of 4 equivalents of phenol and of 1 equivalent of tetramethylsilyl chloride in a mixture of dichloromethane and ethyl acetate. The product formed is isolated from ether.

Hemisuccinates of Testosterone and of Nandrolone
(Precursors 8 and 9)

The steroid is reacted with 1 equivalent of succinic anhydride in a solution of pyridine heated in an autoclave at a temperature of 120° C.

6.3. Addition of a Propionic Arm to Testosterone
and to Nandrolone (Precursors 10 and 11) as well
as to Progesterone (Precursor 12)

The potassium salt of the steroid (nandrolone, testosterone and 11-α-hydroxyprogesterone) is formed by reacting 1 equivalent of steroid with 1 equivalent of potassium tert-butoxide in a tetrahydrofuran medium. After 15 minutes, the medium is diluted with three volumes of dimethylformamide and 1 equivalent of β-propiolactone is added.

6.4. Addition of a Propionic Arm to Estradiol
(Precursor 13)

The estradiol is protected at the level of the phenol by addition of a tert-butyldimethylsilyl group; estradiol and thallium ethoxide, in equivalent quantities, are heated in benzene, continuously removing the alcohol which is liberated by azeotropic distillation. When the reaction is complete, 1.1 equivalent of tert-butyldimethylsilyl chloride is added and the reaction is continued until the substitution of the phenol is complete (precursor 14). The potassium salt of the protected steroid is formed and it is substituted with the propionic chain as described above for precursors 10 to 12.

6.5. Formation of Oxacillin Side Chains by
Reacting Precursors 1 to 5 with Precursors 6 to 14

Precursor 1 is activated in solution in dichloromethane supplemented with a trace of dimethylformamide in the presence of 5 mg % of dimethylaminopyridine and 1 equivalent of either precursor 14, or of nandrolone or of testosterone, or of 11-α-hydroxyprogesterone and of a slight excess of dicyclohexylcarbodiimide gradually added to the solution cooled to 0° C. After removal of the dicyclohexylurea, the product is isolated from petroleum ether. Protection of the 4-isoxazolecarboxylic acid is removed by the action of trifluoroacetic acid in a solution of nitromethane heated under reflux for 40 minutes. The product is purified by chromatography on a silica column eluted with a toluene, ethyl acetate and acetic acid 2;1;0.1 mobile phase. Chains 3, 4, 5 and 6 result from this preparation.

Precursor 1 is activated with isobutyl chloroformate (1.1 equivalent) in dioxane containing a trace of dimethylformamide at a temperature of 0° C. in the presence of a slight excess of triethylamine. A solution, in dimethylformamide, of one of precursors 6 or 7 is added to this solution and the reaction is allowed to proceed in the presence of an excess of triethylamine in order to obtain chains 7 and 8 after deprotection as above.

Any one of precursors 14, nandrolone, testosterone or 11-α-hydroxyprogesterone and thallium ethoxide placed in equivalent quantities in benzene are heated while continuously removing the alcohol which is liberated by distillation of the benzene. When the reaction is complete, 1 equivalent of either precursor 2a or 2b depending on the reactivity, or of precursor 3a or 3b depending on the reactivity is added, and the reaction is continued until complete substitution is obtained. Chains 9 to 16 are obtained by this route after purification on a silica column with, as mobile phase, a mixture of white petrolatum and of toluene having a composition suited to the lipophilicity of the product, and the deprotection is carried out as above.

Any one of precursors 8 to 13 is converted to a tert-butyldimethylsilyl ester by reaction with 1 equivalent of tert-butyldimethylsilyl chloride in the presence of imidazole in a medium consisting of tetrahydrofuran. This ester is reacted in dichloromethane in the presence of oxalyl chloride and catalytic quantities of dimethylformamide in order to form the corresponding acid chloride which is coupled to precursor 4 introduced into the reaction medium in an equivalent quantity. Chains 17 to 22 are produced in this manner after deprotection according to the methods described above. Precursor 5 is converted to an acid chloride in dichloromethane medium by 1 equivalent of oxalyl chloride in the presence of catalytic quantities of dimethylformamide, and reacted with any one of precursors 6, 7 or 14 or any one of the following products: nandrolone, testosterone and 11-α-hydroxyprogesterone introduced into the reaction medium in equivalent quantities. Chains 23 to 38 are obtained after deprotection according to the method already described.

6.6. Coupling of Chains 1 to 26 to 6-APA

The carboxyl at position 4 of the isoxazole ring of the chain is activated with methanesulfonyl chloride (1 equivalent) in tetrahydrofuran medium cooled to −50° C. and containing 1 equivalent of diisopropylethylamine. After reaction and returning to room temperature, 1 equivalent of 6-aminopenicillanic acid, dissolved in an aqueous solution of bicarbonate at 2% and diluted with an equal volume of acetone is introduced into the medium. After removal of the solvents and purification by extraction with ether starting with solutions at pH 2 and pH 8.5, the conjugates 1 to 26 are isolated from white petrolatum. However, the products 3, 9, 13, 22 and 28 must undergo deprotection of the phenol with the HF/KF mixture at pH 5 in a tetrahydrofuran medium.

The characteristics of these conjugates (FIGS. 10 to 13) are presented in Table 9.

Results

1. Measurement of Enzymatic Activity and Assay

The measurements were carried out on β-lactamases from different bacterial strains: *Enterobacter cloacae* P99, *Escherichia coli* and *Citrobacter freundii*, symbolized by: P99, *E. Coli* and *C. Freundii*.

The measurements are divided into four parts. The first part comprises the measurements of enzymatic activity in the presence of variable quantities of reporter substrate (nitrocefin) and of enzyme (in the absence of inhibitor). The second is an evaluation of the inhibitory activity of the inhibitors (Table 9). The third groups together the measurements of enzymatic activity in order to determine the quantity of antibody to be used in the assay. The fourth part comprises the assay of the haptens.

2. Measurement of the Activity of the Enzymes

Figure 14:
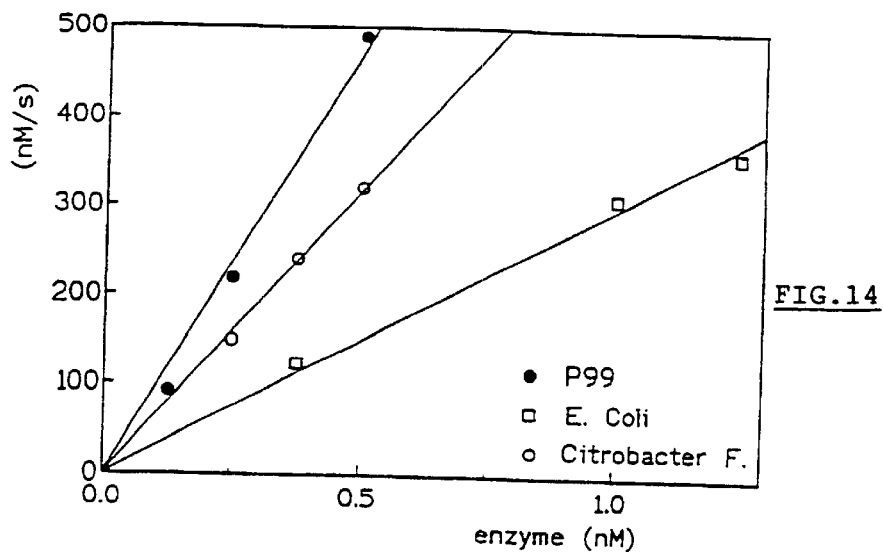
FIG. 14 is the evaluation of enzymatic activity.

The measurements were carried out in the presence of nitrocefin. The objective was the calculation of the catalytic constant of the enzymes, which will serve to determine the quantities of substrate and of enzyme to be used in order to achieve an enzymatic rate compatible with the measurement time. FIG. 14 shows the variation of the maximum rate of the β-lactamases from P99, *E. Coli* and *C. Freundii* ($V_0$) as a function of the enzyme concentration ([E]) and in the presence of nitrocefin (S) at concentrations of 60 μM for the enzymes from P99 and *E. Coli* and of 150 μM for the enzyme from *C. Freundii*. FIG. 14 shows that the enzymatic activities of the P99 and *C. Freundii* enzymes are similar. The catalytic constants ($k_{cat}$) of these two enzymes, calculated based on the graph, are comparable to those in the literature. On the other hand, the enzymatic activity of *E. Coli* appears to be relatively low in relation to the expected value.

3. Measurement of the Inhibitory Activity of Nandrolone Carbenicillinate (I) (Table 3)

By way of example, the results of a selective study carried out on this compound are provided. The results presented in Table 9 give the values obtained according to a similar method. Measurements of the maximum enzymatic rate which were carried out on the enzyme in the presence of nitrocefin and of nandrolone carbenicillinate ($V_1$) served to determine the inhibition constant ($K_i$) of the inhibitor. These measurements determine the concentrations of inhibitor (I) to be used during the assay.

TABLE 3

| Enzyme | [E] (nM) | [S] (μM) | [I] (μM) | $V_1$ (nM/s) | $V_0$ (nM/s) | $V_0/V_1$ -1 | $K_i$ (nM) |
|---|---|---|---|---|---|---|---|
| P99 | 0.0625 | 50 | 0.1 | 36 | 52 | 0.44 | 76 |
|  | 0.0625 | 50 | 0.3 | 20 | 52 | 1.6 | 62 |
|  | 0.0625 | 50 | 0.4 | 17 | 52 | 2.06 | 65 |
|  | 0.0625 | 50 | 0.5 | 16 | 52 | 2.25 | 74 |
|  | 0.25 | 60 | 0.2 | 131 | 218 | 0.66 | 88 |
|  | 0.25 | 60 | 0.24 | 116 | 218 | 0.88 | 78 |
|  |  |  |  |  |  |  | $K_i$ = 74 |
| C. Freundii | 0.375 | 60 | 0.1 | 209 | 240 | 0.15 | 80 |
|  | 0.375 | 60 | 0.2 | 163 | 240 | 0.47 | 62 |
|  |  |  |  |  |  |  | $K_i$ = 71 |
| E. Coli | 1 | 150 | 0.2 | 260 | 310 | 0.19 | 800 |
|  | 1 | 150 | 0.4 | 220 | 310 | 0.41 | 760 |
|  |  |  |  |  |  |  | $K_i$ = 780 |

4. Measurement of the Inhibitory Activity of Nandrolone Carbenicillinate in the Presence of Antibodies (Table 4)

The objective of these measurements, by way of example, is the evaluation of the restoration of the predominant part of the enzymatic activity in the presence of a precise quantity of inhibitor. Table 4 gives the rates of enzymatic reaction ($V_{ab}$) recorded in the presence of β-lactamases, nitrocefin, nandrolone carbenicillinate and anti-nandrolone antibodies. It also shows the dilution factors for the serum containing the antibodies (dil. serum) used in the measurement medium.

TABLE 4

| Enzyme | [S] (nM) | [E] (μM) | [I] (μM) | dil. Serum | $V_{ab}$ (nM/s) | $V_0$ (nM/s) | $V_1$ (nM/S) |
|---|---|---|---|---|---|---|---|
| P99 | 60 | 0.25 | 0.2 | 1000 x | 170 | 218 | 131 |
|  | 60 | 0.25 | 0.2 | 770 x | 189 | 218 | 131 |
|  | 60 | 0.25 | 0.2 | 625 x | 200 | 218 | 131 |
|  | 60 | 0.25 | 0.2 | 500 x | 200 | 218 | 131 |
| E. Coli | 150 | 1 | 0.24 | 714 x | 299 | 310 | 210 |
|  | 150 | 1 | 0.24 | 625 x | 307 | 310 | 210 |
|  | 150 | 1 | 1 | 500 x | 123 | 310 | 90 |
|  | 150 | 1 | 1 | 200 x | 174 | 310 | 90 |
|  | 150 | 1 | 1 | 140 x | 200 | 310 | 90 |
|  | 150 | 1 | 1 | 125 x | 210 | 310 | 90 |
|  | 150 | 1 | 1 | 100 x | 211 | 310 | 90 |

Table b 4shows that for an inhibitor concentration of 0.2 to 0.24 μM, a dilution of a serum of antibodies by a factor of 625 appears to be satisfactory in order to restore a rate close to $V_0$. It also shows that an increase in the inhibitor concentration by a factor of 5 implies an increase in the serum concentration in the same proportion.

5. Assay of Nandrolone (Table 5)

The assay of nandrolone, using the conjugate 1 as inhibitor, was carried out in the following manner: a nandrolone sample is added to a solution of nandrolone carbenicillinate. The mixture thus obtained is complemented with dilute antibody serum and then vortexed for 30 seconds. It is then supplemented with a solution of reporter substrate, buffer and enzyme. After brief stirring, the absorbance of the medium at 482 nm is continuously read for 5 minutes.

Figure 15:
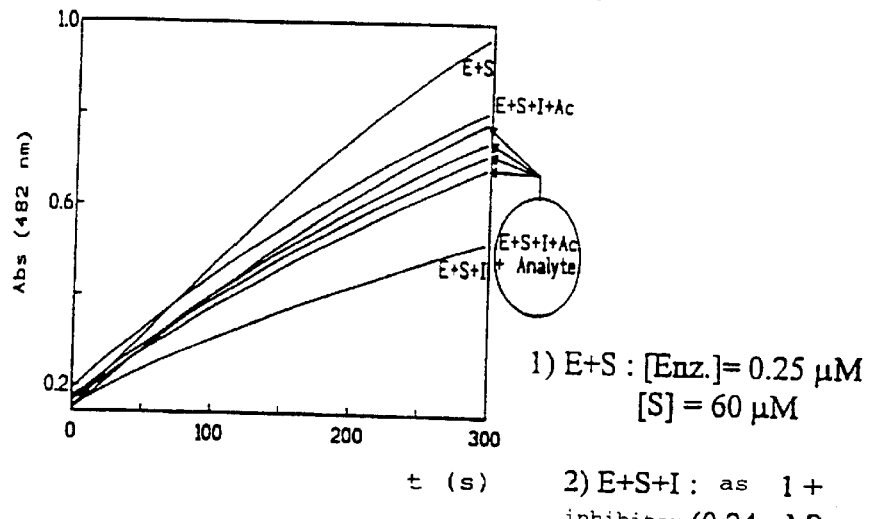
FIG. 15 shows a nandrolone assay.

An example of nandrolone assay is given in FIG. 15. It shows the variation of the absorbance at 482 nm (characteristic wavelength for hydrolyzed nitrocefin) as a function of time. The slope of each straight line gives the rate of the enzymatic reaction. The straight lines on the graph show the variation of the rate with the concentration of free inhibitor. The measurements were carried out in the presence of β-lactamase from P99.

Two examples of nandrolone assay which are presented in Table 5 were carried out respectively with the β-lactamases from P99 and from E. coli. They show that the precision of the assays carried out with the same inhibitor concentration is higher with the β-lactamase from P99. Using the latter, the minimum concentration of nandrolone detectable in the measurement medium is of the order of 0.02 μM, which corresponds to 10 picomoles of substance (measurement volume=500 μl). The minimum concentration detectable using the β-lactamase from E. coli is difficult to determine because of the imprecision of the measurements carried out with concentrations of less than 0.05 μM (that is to say a quantity of 25 picomoles).

TABLE 5

| [E] (μM) | [I] (μM) | dil. serum | [Nan] (μM) | $V_{dos}$ (nM/s) | $V_{ab}$ (nM/s) | $V_i$ (nM/s) |
|---|---|---|---|---|---|---|
| Assay with the β-lactamase from P99 | | | | | | |
| 60 | 0.25 | 0.24 | 625 | 0.02 | 186 | 190 | 116 |
| 60 | 0.25 | 0.24 | 625 | 0.08 | 174 | 190 | 116 |
| 60 | 0.25 | 0.24 | 625 | 0.16 | 161 | 190 | 116 |
| 60 | 0.25 | 0.24 | 625 | 0.20 | 152 | 190 | 116 |
| Assay with the β-lactamase from E. coli | | | | | | |
| 150 | 1 | 0.24 | 625 | 0.05 | 293 | 307 | 250 |
| 150 | 1 | 0.24 | 625 | 0.10 | 283 | 307 | 250 |
| 150 | 1 | 0.24 | 625 | 0.24 | 279 | 207 | 250 |

Figure 16:
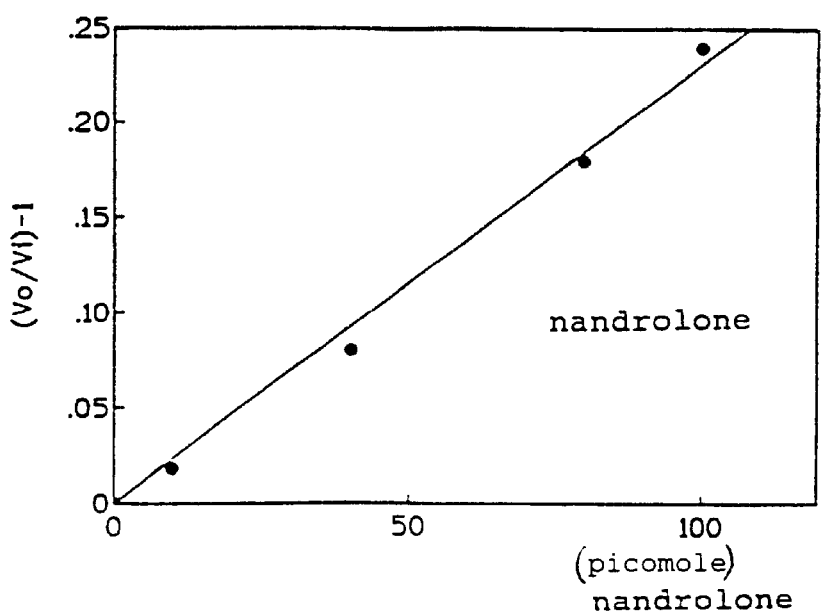
FIG. 16 shows the variation of $[(V_0/V_1)-1]$ as a function of nandrolone.

FIG. 16, which describes the variation of $[(V_0/V_1)-1]$ as a function of the quantity of nandrolonte, shows a linear relationship between the two parameters.

An assay with the β-lactamase from E. Coli carried out with an inhibitor concentration of 1 μM and an adequate quantity of antibody shows that the assay "range" with this enzyme can be increased and is accompanied by a decrease in sensitivity. It is therefore important to optimize the quantity of inhibitor with the aim of achieving the best compromise.

6. Calculation of the Quantity of Substrate and of Enzyme Necessary for the Assay Knowing the measurement time for the assay, it is possible to evaluate from the $k_{cat}$ the quantities of enzyme and substrate used during the assays. For example, for the assays presented above, a measurement time of 5 minutes was set. During these 5 minutes (dt), the absorbance at 482 nm (maximum absorbance of hydrolyzed nitrocefin) should ideally increase by one unit (dA=1) in the absence of enzymatic inhibition. For the P99 enzyme ($k_{cat}$=780 s$^{-1}$), it is desirable to observe a dA/dt=1/300 (s$^{-1}$) which results, taking into account the coefficient of extinction for hydrolyzed nitrocefin ($\epsilon$=15,000 M$^{-1}$ cm$^{-1}$), in a hydrolysis rate:

$$V_0 = dA/dt = 1/(300 \times 15,000) = 2.2 \times 10^{-7} Ms^{-1}$$

On the other hand, it is accepted for the β-lactamases that:

$$V_0 = k_{cat}[E]$$

which implies that:

$$k_{cat}[E] = 2.2 \times 10^{-7} \text{ Ms}^{-1}$$

$$[E] = 2.2 \, 10^7/780 = 2.80 \times 10^{-10} \text{ M}$$

This concentration is close to the ideal concentration determined experimentally (2.5 $10^{-10}$ M).

The minimum concentration of substrate to cover the needs of the assay can also be evaluated. It is known that during the assay time (300 s), a product concentration corresponding to $V_0$ dt is generated in the, medium, that is to say a concentration of $300*2.2 \times 10^{-7} \approx 65 \times 10^{-6}$ M. This value corresponds approximately to 60 μM substrate used during the assays. A slightly higher substrate concentration should be used in order to ensure a maximum rate by saturation with substrate. On the other hand, it is important to limit this concentration in order to maintain a $K_m/(K_m+[S])$ ratio close to one.

7. Calculation of the Quantity of Inhibitor to be Used and Sensitivity of the Assay All the theoretical calculations relating to the quantity of inhibitor to be used and the sensitivity of the assay can be carried out using the equation:

$$\frac{V_o}{V_i} = 1 + \frac{K_m}{K_m + [S]} \frac{[I]}{K_i}$$

The quantity of inhibitor to be used in the assay depends on the inhibition constant $K_i$. The smaller the latter, the lower the quantity of inhibitor necessary to observe a variation in the enzymatic rate which is detectable.

An inhibitor concentration leading to a 50% reduction in the enzymatic activity appears to be a good basis for carrying out an assay. The calculation in the case of an assay with the enzyme from P99 in the presence of nandrolone carbenicillinate ($K_i$=70 nM), using the substrate concentration calculated above (65 μM), is the following:

$$\frac{V_o}{V_i} = 2 = 1 + \frac{25}{25 + 65} \frac{[I]}{70}$$

$$[I] = 240 \text{ nM}$$

This value corresponds to the concentration used during the assay of nandrolone with the β-lactamase from P99.

If it is assumed that it is possible to easily detect a 10% variation in the enzymatic rate, it is possible to detect a quantity of inhibitor equal to:

$$[I] = \left(\frac{V_o}{V_1} - 1\right)\left(\frac{K_m + [S]}{K_m}\right) K_i$$

$$[I] = (1.1 - 1)\left(\frac{25 + 65}{25}\right) 70$$

$$[I] = 24 \text{ nM}$$

In the case of an assay of nandrolone, using a quantity of inhibitor in the presence of a stoichiometric quantity of antibody, it is possible to evaluate the concentration of nandrolone necessary to displace the inhibitor from its immunological complex and to obtain a free inhibitor concentration of 24 nM. In the case where nandrolone has an affinity for the antibody which is of the same order of magnitude as the inhibitor, the Scatchard theory shows that a nandrolone concentration of 24 nM displaces the inhibitor until a practically equivalent free inhibitor concentration is obtained. The detection limit for a volume of 500 μl is consequently $$20 \times 10^{-9} * 500 \times 10^{-6} = 10 \times 10^{-12} \text{ mole}$$

This value is confirmed experimentally by the graph of the assay of nandrolone representing $(V_0/V_1)-1$ as a function of the quantity of nandrolone.

The assays carried out show that it is possible to assay a hapten without carrying out an incubation step. The total duration of a measurement does not exceed 7 to 8 minutes. The limit of detection of the nandrolone of the β-lactamase from P99/nandrolone carbenicillinate/nitrocefin/antibody system is 10 pico-moles.

The sensitivity is highly improved by the use of nandrolone oxacillinate, because the $K_i$ values for oxacillin (0.5 nM) are more advantageous than those for carbenicillin (10 nM)

Results of the same order are obtained with theophylline carbenicillinate, whose kinetic characteristics ($K_i$) are sufficient to be commercially exploited in an assay.

8. Examples of Protecting Agents

Table 6 shows that the rate of hydrolysis of the substrate is influenced by the presence of serum. In the absence of enzyme, rates of hydrolysis of the substrate (nitrocefin) varying with the percentage of serum present in the measurement medium are observed. Table 6 shows that the addition of sodium acid [sic] ($NaN_3$) or of phenylbutazone 0.07 mg/ml highly reduces this rate. Furthermore, the addition of phenylbutazone 0.07 mg/ml improves the quality of the assay by increasing the availability of the substrate. Examples of assay of nandrolone in the presence of these two protecting agents are given in this table.

TABLE 6

| Vol Mes (μl) | V (μM/s) | Qenz (nM) | Qsub (nM) | Qinh (nM) | Qanal (nM) | DSA | % serum | Treatment | Buffer | pH |
|---|---|---|---|---|---|---|---|---|---|---|
| 500 | 0.219 | 0.25 | 75 | — | — | — | 0 | — | hepes 2.5 mM | 8.2 |
| 500 | 0.143 | 0.25 | 75 | 240 | — | — | 0 | — | hepes 2.5 mM | 8.2 |

TABLE 6-continued

| Vol Mes (µl) | V (µM/s) | Qenz (nM) | Qsub (nM) | Qinh (nM) | Qanal (nM) | DSA | % serum | Treatment | Buffer | pH |
|---|---|---|---|---|---|---|---|---|---|---|
| 500 | 0.206 | 0.25 | 75 | 240 | — | 625 | 0 | — | hepes 2.5 nM | 8.2 |
| 500 | 0.14 | — | 75 | — | — | — | 24 | — | hepes 2.5 mM | 8.2 |
| 500 | 0.05 | — | 75 | — | — | — | 2 | — | hepes 2.5 mM | 8.2 |
| 500 | 0.203 | 0.25 | 75 | — | — | — | 2 | — | hepes 2.5 mM | 8.2 |
| 500 | 0.156 | 0.25 | 75 | 240 | — | — | 2 | — | hepes 2.5 mM | 8.2 |
| 500 | 0.215 | 0.25 | 75 | 240 | — | 625 | 2 | — | hepes 2.5 mM | 8.2 |
| 500 | 0.220 | 0.25 | 75 | — | — | — | 0 | — | hepes 2.5 mM | 8.2 |
| 500 | 0.110 | 0.25 | 75 | 300 | — | — | 0 | — | hepes 2.5 mM | 8.2 |
| 500 | 0.197 | 0.25 | 75 | 300 | — | 500 | 0 | — | hepes 2.5 mM | 8.2 |
| 500 | 0.196 | 0.25 | 75 | 300 | — | 454 | 0 | — | hepes 2.5 mM | 8.2 |
| 500 | 0.188 | 0.25 | 75 | 300 | — | 556 | 0 | — | hepes 2.5 mM | 8.2 |
| 500 | 0.148 | 0.25 | 75 | 300 | — | 500 | 2 | — | hepes 2.5 mM | 8.2 |
| 500 | 0.134 | 0.25 | 75 | 300 | 110 | 500 | 2 | — | hepes 2.5 mM | 8.2 |
| 500 | 0.127 | 0.25 | 75 | 300 | 400 | 500 | 2 | — | hepes 2.5 mM | 8.2 |
| 500 | 0.111 | 0.25 | 75 | 300 | 2000 | 500 | 2 | — | hepes 2.5 mM | 8.2 |
| 500 | 0.015 | — | 75 | — | — | — | 2 | Tp PBS + azide 0.1% | hepes/phos | 7 |
| 500 | 0.101 | 0.25 | 75 | 300 | — | — | 2 | Tp PBS + azide 0.1% | hepes/phos | 7 |
| 500 | 0.193 | 0.25 | 75 | — | — | — | 2 | Tp PBS + azide 0.1% | hepes/phos | 7 |
| 500 | 0.192 | 0.25 | 75 | 300 | — | 500 | 2 | Tp PBS + azide 0.1% | hepes/phos | 7 |
| 500 | 0.170 | 0.25 | 75 | 300 | 22 | 500 | 2 | Tp PBS + azide 0.1% | hepes/phos | 7 |
| 500 | 0.165 | 0.25 | 75 | 300 | 110 | 500 | 2 | Tp PBS + azide 0.1% | hepes/phos | 7 |
| 500 | 01.35 | 0.25 | 75 | 300 | 400 | 500 | 2 | Tp PBS + azide 0.1% | hepes/phos | 7 |
| 500 | 0.125 | 0.25 | 75 | 300 | 2000 | 500 | 2 | Tp PBS + azide 0.1% | hepes/phos | 7 |
| 450 | 0.12 | — | 75 | — | — | — | 10 | — | citrate 0.005 M | 7 |
| 450 | 0.022 | — | 75 | — | — | — | 10 | phenylbutazole 0.07 mg | citrate 0.005 M | 7 |
| 450 | 0.276 | 0.75 | 75 | — | — | — | 10 | phenylbutazole 0.07 mg | citrate 0.005 M | 7 |
| 450 | 0.246 | 0.75 | 75 | 275 | — | — | 10 | phenylbutazole 0.07 mg | citrate 0.005 M | 7 |
| 450 | 0.215 | 0.75 | 75 | 275 | 11 | 500 | 10 | phenylbutazole 0.07 mg | citrate 0.005 M | 7 |
| 450 | 0.207 | 0.75 | 75 | 275 | 22 | 500 | 10 | phenylbutazole 0.07 mg | citrate 0.005 M | 7 |
| 450 | 0.184 | 0.75 | 75 | 275 | 110 | 500 | 10 | phenylbutazole 0.07 mg | citrate 0.005 M | 7 |

Legend
Vol. Mes.: Final volume in which the enzymatic kinetics is monitored
V: Rate of degradation of the substrate (nitrocefin)
Oenz: Concentration of P99 β-lactamase in the final volume
Osub: Concentration of nitrocefin in the final volume
Oinh: Concentration of inhibitor in the final volume
Oanal: Concentration of analyte in the final volume
DSA: Dilution of the serum containing the antinandrolone antibodies
% serum: Percentage of serum in the final volume
Tm: Protecting agent tested (PBS = 0.1 M phosphate buffer + 0.15 M NaCl)
Buffer: Buffer used during the measurements (hepes/phos = 9/1 mixture of PBS buffer and of Hepes buffer 2.5 mM)
pH: pH of the buffer used during the measurements The abovementioned iodine-starch assay method based on the generation of iodine in a solution of starch paste stabilized for [sic] cadmium iodide finds application in the assay of other antibiotics.

9. Assay of Cephalexin (Table 7)

100 ml of a mixed solution of 0.003 N cadmium iodide and 0.00275 N potassium iodate are prepared by dissolving, respectively, 54.92 mg of cadmium iodide and 9.77 mg of potassium iodate in a hepes buffer solution pH 8.2 (10 mM) charged with 1% starch paste. 100 ml of 0.2 M DTPA solution in hepes buffer are also prepared. Finally, a 1 mM stock solution of cephalexin is prepared by dissolving 34 mg of cephalexin in 100 ml of the hepes buffer described above.

Preparation of the Scale the stock solution of cephalexin is hydrolyzed and diluted by collecting 1 ml which is treated with 4 ml of 0.001 M sodium hydroxide for 15 minutes, and then adjusted to 100 ml with the hepes buffer;
a starch iodine solution is prepared by collecting 20 ml of mixed solution, 25 ml of DTPA and 3 ml of glacial acetic acid, and then the volume is adjusted with hepes buffer (starch iodine solution);
a hydrolyzed cephalexin concentration scale from 1 to 6 µM is prepared by removing volumes of 100 to 600:1 to which 100 µl of the starch iodine solution are added. The volume is adjusted to 1 ml with hepes buffer;
the final absorbance of the solutions is measured after 5 minutes at 620 nm.

TABLE 7

| Concentrations (:M) | Absorbance |
|---|---|
| 0 | 0.963 |
| 1 | 0.831 |
| 2 | 0.682 |
| 3 | 0.549 |
| 4 | 0.428 |
| 5 | 0.280 |
| 6 | 0.155 |

There are obtained a correlation coefficient of 0.9961 and an equation of a straight line $$Y = -0.1345 X + 0.96$$

Assay cephalexin is diluted so as to obtain a concentration of between 0.5 and 2 mm;

the preceding solution is hydrolyzed and diluted according to the technique used for the preparation of the scale;

250 µl of the hydrolyzed solution of cephalexin are collected, 100 µl of starch iodine solution are added and the volume is adjusted to 1 ml with hepes buffer;

after 5 minutes, the absorbance is read at 620 nm and the concentration is calculated relative to the pre-established scale.

10. Assay of Nandrolone Using Nandrolone Cabenicillate (Conjugate 1) and the Cephalexin-iodine-starch Mixture as Reporter Substrate with the β-lactamase from P99 (Table 8)

TABLE 8

| S (µM) | [E] (µM) | [I] (µM) | dil. serum | [Nan] (µM) | $V_{dos}$ (nM/s) | $V_{ab}$ (nM/s) | $V_i$ (nM/s) |
|---|---|---|---|---|---|---|---|
| 20 | 1 | 0.15 | 1000 | 0.0125 | 43 | 45 | 28.5 |
| 20 | 1 | 0.15 | 1000 | 0.05 | 36.3 | 45 | 28.5 |
| 20 | 1 | 0.15 | 1000 | 0.1 | 30.9 | 45 | 28.5 |
| 20 | 1 | 0.15 | 1000 | 0.125 | 28.4 | 45 | 28.5 |

The variation in color is observed at 620 nm which corresponds to an iodine consumption of the cephalexin degraded during the measuring process. The iodine is generated in the following manner: 100 µl of a mixed solution of starch cadmium iodide and of potassium iodate (0.002 N $CdI_2$—0.0024 N $KIO_3$—1.5% starch) are removed. 100 µl of a 0.1 N solution of sodium salt of DTPA are added to this solution and the pH is brought to 2 by addition of 1 M HCl. after [sic] reaction, the medium is brought to pH 7 by addition of a sufficient quantity of 0.02 M Hepes buffer and then it is brought to the final volume of 900 µl after having introduced the homogeneous immunoassay reagents.

TABLE 9

Characteristics of the carbenicillin and oxacillin conjugates

| Conjugate | Mass PP | IR $v_1$ | $v_2$ | $v_3$ | $v_4$ | $v_5$ | $K_i^x$ (nM) |
|---|---|---|---|---|---|---|---|
| 1 | 635*+ | 1765 | 1740 | 1725 | 1682 | 1676 | 70 ± 43 |
| 2 | 694*+ | 1764 | 1752 | 1721 | 1673 |  | 84 ± 47 |
| 3 | 699*+ | 3294 | 1776 | 1716 | 1654 |  | 24 ± 26 |
| 4 | 699x− | 1767 | 1726 | 1717 | 1677 | 1664 | 18 ± 23 |
| 5 | 714x− | 1788 | 1717 | 1674 | 1638 | 1279 | 22 ± 19 |
| 6 | 759*+ | 1767 | 1744 | 1722 | 1699 | 1674 | 19 ± 27 |
| 7 | 802*+ | 1781 | 1746 | 1719 | 1673 |  | 23 ± 18 |
| 8 | 816*+ | 1766 | 1738 | 1724 | 1680 | 1662 | 17 ± 21 |
| 9 | 751*+ | 3302 | 1764 | 1726 | 1668 |  | 14 ± 17 |
| 10 | 753*+ | 1763 | 1725 | 1683 | 1668 |  | 12 ± 14 |
| 11 | 767*+ | 1786 | 1718 | 1675 | 1641 |  | 15 ± 16 |
| 12 | 809*+ | 1765 | 1723 | 1702 | 1668 |  | 20 ± 21 |
| 13 | 758*+ | 3299 | 1786 | 1717 | 1672 |  | 18 ± 23 |
| 14 | 760*+ | 1783 | 1720 | 1677 |  |  | 28 ± 22 |
| 15 | 774*+ | 1769 | 1726 |  |  |  | 26 ± 27 |
| 16 | 816*+ | 1764 | 1726 | 1711 | 1670 |  | 21 ± 24 |
| 17 | 788*+ | 1784 | 1739 | 1720 | 1668 |  | 23 ± 19 |
| 18 | 774*+ | 1785 | 1742 | 1718 | 1671 |  | 21 ± 24 |
| 19 | 760*+ | 1787 | 1718 | 1680 |  |  | 29 ± 27 |
| 20 | 746*+ | 1784 | 1717 | 1678 |  |  | 30 ± 33 |
| 21 | 802*+ | 1763 | 1722 | 1703 | 1670 |  | 25 ± 23 |
| 22 | 744*+ | 3307 | 1721 | 1667 |  |  | 19 ± 21 |
| 23 | 761*+ | 1768 | 1750 | 1722 | 1676 |  | 21 ± 26 |
| 24 | 747*+ | 1766 | 1742 | 1724 | 1683 | 1674 | 28 ± 31 |
| 25 | 846*+ | 1764 | 1745 | 1724 | 1671 |  | 29 ± 26 |
| 26 | 860*+ | 1766 | 1740 | 1725 | 1669 |  | 23 ± 25 |
| 27 | 803*+ | 1765 | 1741 | 1726 | 1710 | 1674 | 26 ± 25 |
| 28 | 745*+ | 3306 | 1765 | 1743 | 1724 | 1677 | 21 ± 24 |

Legend
Column 2
*: FAB
+: M + H
−: M − H
Column 8
x: calculated using P99

11. Assay of Nandrolone and of Progesterone Using the Oxacillinates of these two Steroids as Inhibitor (Conjugates 4 and 6)

Figure 17:
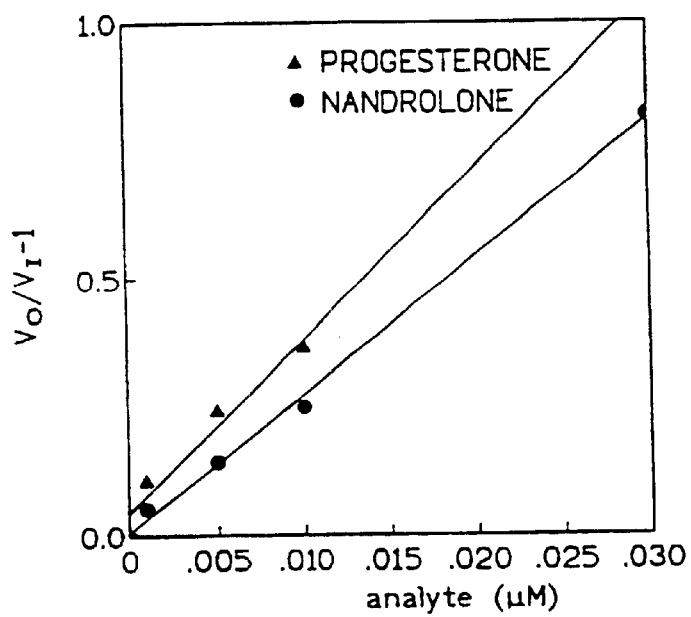
FIG. 17 shows the variation of $[(V_0/V_1)-1]$ as a function of nandrolone and as a function of progesterone.

This assay is carried out as mentioned in Example 5, and is represented in Table 10 as well as in FIG. 17.

TABLE 10

| [S] (µM) | [E] (µM) | [I] (µM) | dil. serum | [Nan] (µM) | $V_{dos}$ (nM/s) | $V_{ab}$ (nM/s) | $V_i$ (nM/s) |
|---|---|---|---|---|---|---|---|
| Assay of nandrolone in the presence of nandrolone oxacillinate | | | | | | | |
| 60 | 0.25 | 0.034 | 4375 | 0.001 | 190 | 200 | 110 |
| 60 | 0.25 | 0.034 | 4375 | 0.005 | 175 | 200 | 110 |
| 60 | 0.25 | 0.034 | 4375 | 0.010 | 160 | 200 | 110 |
| 60 | 0.25 | 0.034 | 4375 | 0.030 | 110 | 200 | 110 |
| Assay of progesterone in the presence of progesterone oxacillinate | | | | | | | |
| 60 | 0.25 | 0.034 | 7450 | 0.001 | 185 | 205 | 105 |
| 60 | 0.25 | 0.034 | 7450 | 0.005 | 165 | 205 | 105 |
| 60 | 0.25 | 0.034 | 7450 | 0.010 | 150 | 205 | 105 |
| 60 | 0.25 | 0.034 | 7450 | 0.030 | 100 | 205 | 105 |

What is claimed is:

1. Method for detecting and/or quantifying a hapten in a homogeneous phase comprising the steps of:

contacting a known quantity of an inhibitor-hapten conjugate with a sample solution containing the hapten to be detected or quantified;

adding a quantity of anti-hapten antibody corresponding exactly to the quantity of the inhibitor-hapten conjugate in solution, said antibody binding competitively to the hapten and to the inhibitor-hapten conjugate;

adding to the solution an unconjugated type C β-lactamase having an active site for two substrates entering into competition on said active site, the first substrate being a reporter substrate transforming into a product detectable or quantifiable by UV/visible radiation measurement, the second substrate being the antibody-unbound inhibitor-hapten complex modulating the rate of hydrolysis of the reporter substrate; and detecting or quantifying by UV/visible radiation measurement the concentration of the product resulting from the transformation of the reporter substrate wherein the $K_m$ constant for the reporter substrate is at least 100 times higher than the $K_i$ constant for the inhibitor-hapten conjugate, and the $k_{cat}$ constant for the reporter substrate is at least 10 times higher than the $k_{cat}$ constant for the inhibitor-hapten conjugate,
wherein $K_m$ is equal to the reporter substrate concentration, expressed in molarity (M), at which half the maximum reaction rate of β-lactamase is obtained, $K_i$ reflects the affinity of the inhibitor for the enzyme and is equal to the $K_m$ for the inhibitor-hapten conjugate, expressed in molarity (M), and $k_{cat}$ is the number of times each β-lactamase molecule hydrolyses one molecule of reporter substrate per unit of time, expressed in $sec^{-1}$.

2. The method according to claim 1, further comprising the step of contacting the solution containing the hapten to be assayed with substances selected from the group consisting of agents for protecting β-lactamase, agents for protecting the reporter substrate, agents for protecting the hapten-inhibitor complex or decontaminating agents to remove possible interferences prior to adding the inhibitor-hapten complex, the antibody, and the type C β-lactamase.

3. The method according to claim 1, wherein the $k_{cat}$ constant for the reporter substrate is greater than 0.1 $s^{-1}$.

4. The method according to claim 1, wherein the $K_i$ and $k_{cat}$ constants for inhibitor-hapten complex are less than 100–5000 µM and less than 0.1 $s^{-1}$, respectively.

5. The method according to claim 1, wherein the type C β-lactamase is chosen from the group consisting of the β-lactamases obtained from *Enterobacter cloacae* Q908R and P99, from *Citrobacter freundii* and from *Escherichia coli*.

6. The method according to claim 1, wherein the inhibitor and the reporter substrate are chosen from the group consisting of the penicillins, the cephalosporins and the β-lactam antibiotics.

7. The method according to claim 6, wherein the reporter substrate is chosen from the group consisting of cephaloridine, nitrocefin, cephalothin, cephalexin, cephalosporin C, cephacetrile and cefazolin.

8. The method according to claim 1, wherein the transformation of the reporter substrate is detected by a starch-iodine color system.

9. The method according to claim 6, wherein the inhibitor is chosen from the group consisting of carbenicillin, oxacillin, cefuroxine, cefotaxime and methicillin.

10. The method according to according to claim 1, wherein the hapten is chosen from the group consisting of hormones, anabolic steroids and drugs.

11. The method according to claim 1, wherein the hapten is chosen from the group consisting of testosterone, estridiol, progesterone, aldosterone, cortisol, methylamphetamine, methadone, tetrahydrocannabinol, $\Delta^4$-androstenedione, morphine, DHEA sulfate, nandrolone, theophylline, cocaine and each of their corresponding hydrolysis derivatives.

* * * * *